(12) United States Patent
Antaki

(10) Patent No.: US 11,672,968 B2
(45) Date of Patent: Jun. 13, 2023

(54) BLOOD-IMMERSED BEARING SYSTEM FOR A BLOOD PUMP

(71) Applicant: James F. Antaki, Pittsburgh, PA (US)

(72) Inventor: James F. Antaki, Pittsburgh, PA (US)

(73) Assignee: Carnegie Mellon University, Pittsburgh, PA (US)

(*) Notice: Subject to any disclaimer, the term of this patent is extended or adjusted under 35 U.S.C. 154(b) by 0 days.

(21) Appl. No.: 16/638,180

(22) PCT Filed: Aug. 10, 2018

(86) PCT No.: PCT/US2018/046291
§ 371 (c)(1),
(2) Date: Feb. 11, 2020

(87) PCT Pub. No.: WO2019/033012
PCT Pub. Date: Feb. 14, 2019

(65) Prior Publication Data
US 2020/0368415 A1 Nov. 26, 2020

Related U.S. Application Data

(60) Provisional application No. 62/605,402, filed on Aug. 11, 2017.

(51) Int. Cl.
*A61M 60/82* (2021.01)
*A61M 60/148* (2021.01)
(Continued)

(52) U.S. Cl.
CPC .......... *A61M 60/82* (2021.01); *A61M 60/148* (2021.01); *A61M 60/165* (2021.01);
(Continued)

(58) Field of Classification Search
CPC .............. A61M 60/148; A61M 60/205; A61M 60/422; A61M 60/50; A61M 60/818;
(Continued)

(56) References Cited

U.S. PATENT DOCUMENTS 5,588,812 A * 12/1996 Taylor ................. F04D 29/0413
417/356
5,695,471 A * 12/1997 Wampler ................. H02K 7/09
604/131
(Continued)

FOREIGN PATENT DOCUMENTS

EP 3069740 9/2016

OTHER PUBLICATIONS

Antaki et al., "An improved left ventricular cannula for chronic dynamic blood pump support," Artificial Organs, 1995, 19(7):671-675.
(Continued)

*Primary Examiner* — Eric J Zamora Alvarez
(74) *Attorney, Agent, or Firm* — Fish & Richardson P.C.

(57) ABSTRACT

A blood pump includes a housing having an inlet. A rotor disposed in the housing and configured to rotate substantially about the axis to pump blood from the inlet to the outlet. A stator is disposed within the housing and configured to drive rotation of the rotor about the axis. A bearing mechanism for supporting the rotor inside the housing includes a magnetic bearing configured to magnetically support the rotor inside the housing in a radial direction from the axis. The bearing mechanism includes a sliding bearing configured to physically support the rotor inside the housing in an axial direction along the axis of the housing and allow rotation of the rotor substantially about the axis, the sliding bearing comprising at least one point of contact where the rotor is configured to physically contact a trunnion affixed to the housing.

20 Claims, 13 Drawing Sheets

(51) Int. Cl.

| | |
|---|---|
| *A61M 60/165* | (2021.01) |
| *A61M 60/216* | (2021.01) |
| *A61M 60/422* | (2021.01) |
| *A61M 60/508* | (2021.01) |
| *A61M 60/824* | (2021.01) |
| *A61M 60/825* | (2021.01) |
| *A61M 60/857* | (2021.01) |
| *F04D 29/046* | (2006.01) |
| *F04D 29/051* | (2006.01) |
| *F04D 29/048* | (2006.01) |
| *F04D 29/041* | (2006.01) |

(52) U.S. Cl.
CPC ........ *A61M 60/216* (2021.01); *A61M 60/422* (2021.01); *A61M 60/508* (2021.01); *A61M 60/824* (2021.01); *A61M 60/825* (2021.01); *A61M 60/857* (2021.01); *F04D 29/0465* (2013.01); *F04D 29/051* (2013.01); *F05D 2240/511* (2013.01); *F05D 2240/515* (2013.01); *F05D 2240/52* (2013.01)

(58) Field of Classification Search
CPC . A61M 60/82; A61M 60/825; F04D 29/0413; F04D 29/0467; F04D 29/048; F16C 17/10; F16C 2316/18; F16C 32/0425
See application file for complete search history.

(56) References Cited

U.S. PATENT DOCUMENTS

| | | | | |
|---|---|---|---|---|
| 5,707,218 | A * | 1/1998 | Maher | F04D 13/0646 417/356 |
| 5,840,070 | A * | 11/1998 | Wampler | F16C 39/063 604/131 |
| 6,071,093 | A * | 6/2000 | Hart | H02K 7/14 417/424.2 |
| 6,093,001 | A * | 7/2000 | Burgreen | F04D 29/0467 417/423.8 |
| 6,186,665 | B1 * | 2/2001 | Maher | F04D 29/0467 384/206 |
| 6,244,835 | B1 | 6/2001 | Antaki et al. | |
| 6,254,359 | B1 * | 7/2001 | Aber | F04D 29/0465 417/356 |
| 6,447,266 | B2 | 9/2002 | Antaki et al. | |
| 6,742,999 | B1 | 6/2004 | Nusser et al. | |
| 6,861,778 | B2 | 3/2005 | Zraelev et al. | |
| 7,762,941 | B2 * | 7/2010 | Jarvik | F04D 29/0467 600/16 |
| 8,864,643 | B2 * | 10/2014 | Reichenbach | A61M 60/205 600/16 |
| 9,144,638 | B2 * | 9/2015 | Zimmermann | F16C 17/10 |
| 9,265,870 | B2 * | 2/2016 | Reichenbach | A61M 25/005 |
| 10,029,038 | B2 * | 7/2018 | Hodges | A61M 60/419 |
| 10,195,324 | B2 * | 2/2019 | Foster | A61M 60/818 |
| 10,842,921 | B2 * | 11/2020 | Siess | A61M 60/818 |
| 10,851,802 | B2 * | 12/2020 | Furukawa | F04D 29/628 |
| 10,857,273 | B2 * | 12/2020 | Hodges | A61M 60/818 |
| 2008/0269880 | A1 | 10/2008 | Jarvik | |
| 2011/0237863 | A1 | 9/2011 | Ricci et al. | |
| 2013/0121821 | A1 * | 5/2013 | Ozaki | F04D 29/041 415/205 |
| 2015/0152915 | A1 | 6/2015 | Peterson | |
| 2015/0285258 | A1 * | 10/2015 | Foster | F04D 17/10 415/203 |
| 2016/0144089 | A1 * | 5/2016 | Woo | A61M 60/40 417/423.1 |

OTHER PUBLICATIONS

Paden et al., "Design formulae for permanent magnet bearings," ASME J Mechanical Design, 2003, 125:734-738.
PCT International Preliminary Report on Patentability in International Appln. No. PCTUS2018046291, dated Feb. 20, 2020, 11 pages.
PCT Search Report and Written Opinion in International Appln. No. PCT/US18/46291, dated Oct. 24, 2018, 15 pages.
Starling et al., "Unexpected Abrupt Increase in Left Ventricular Assist Device Thrombosis," N. Engl. Med., 2014, 370(1):370-33-40.

* cited by examiner

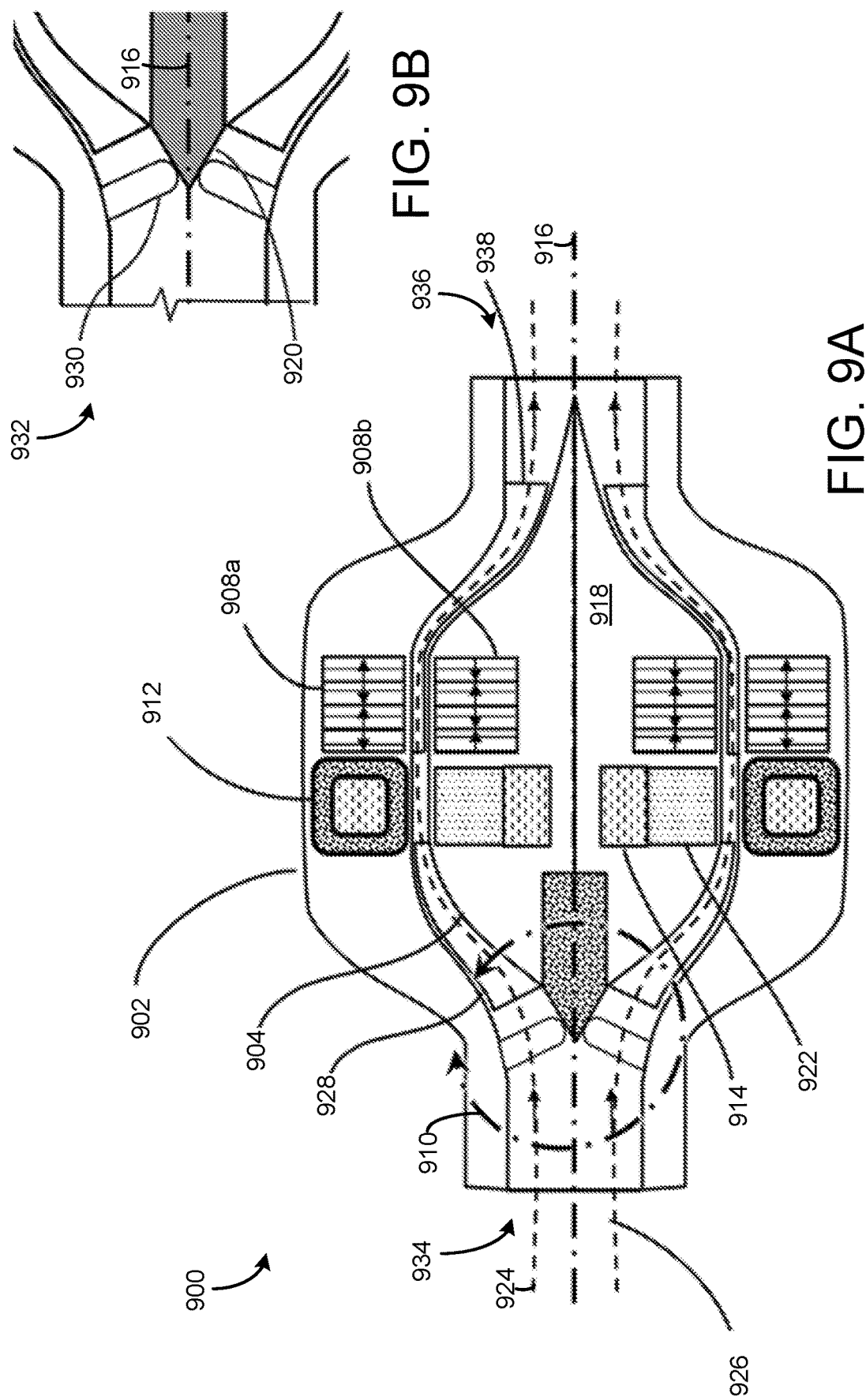

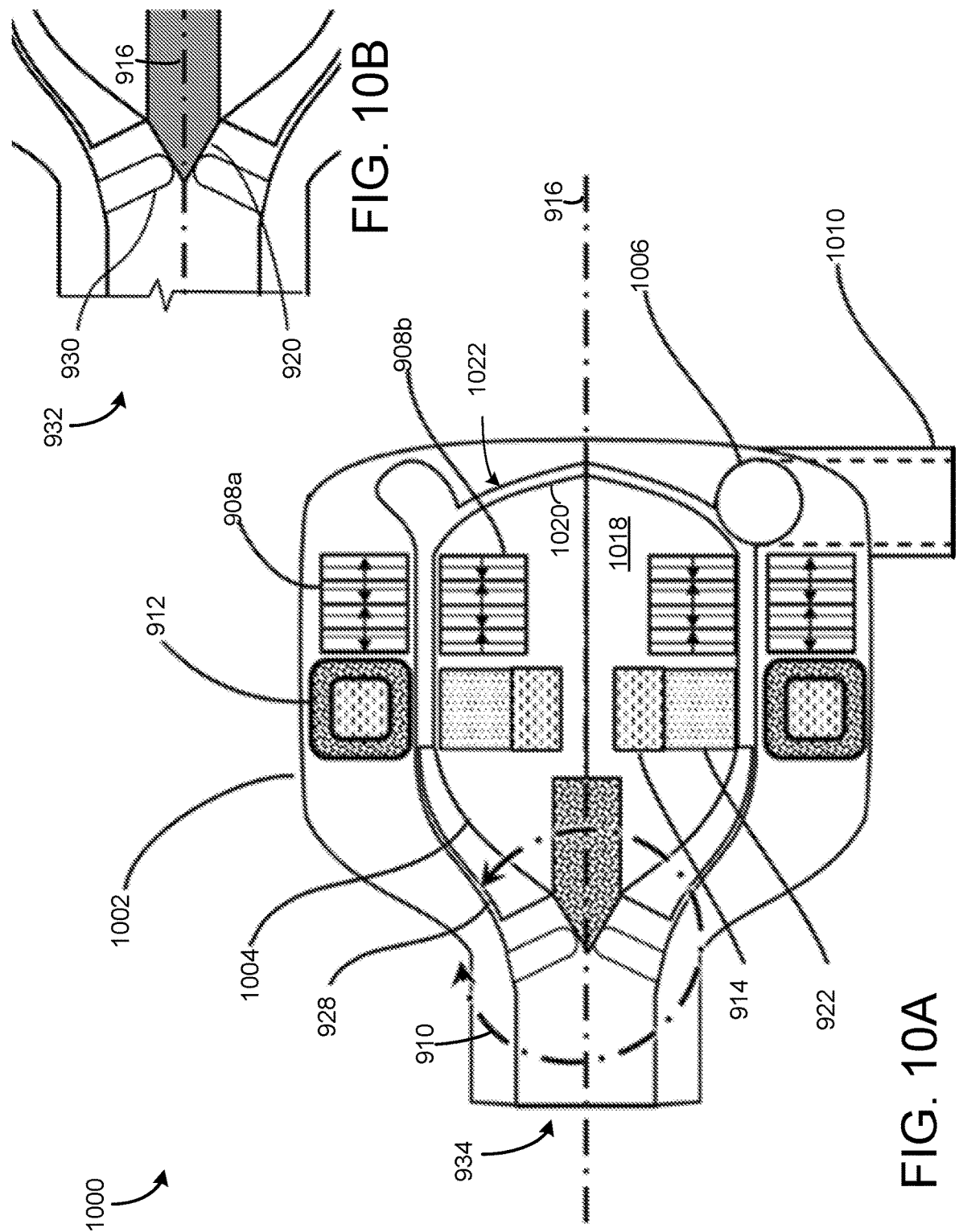

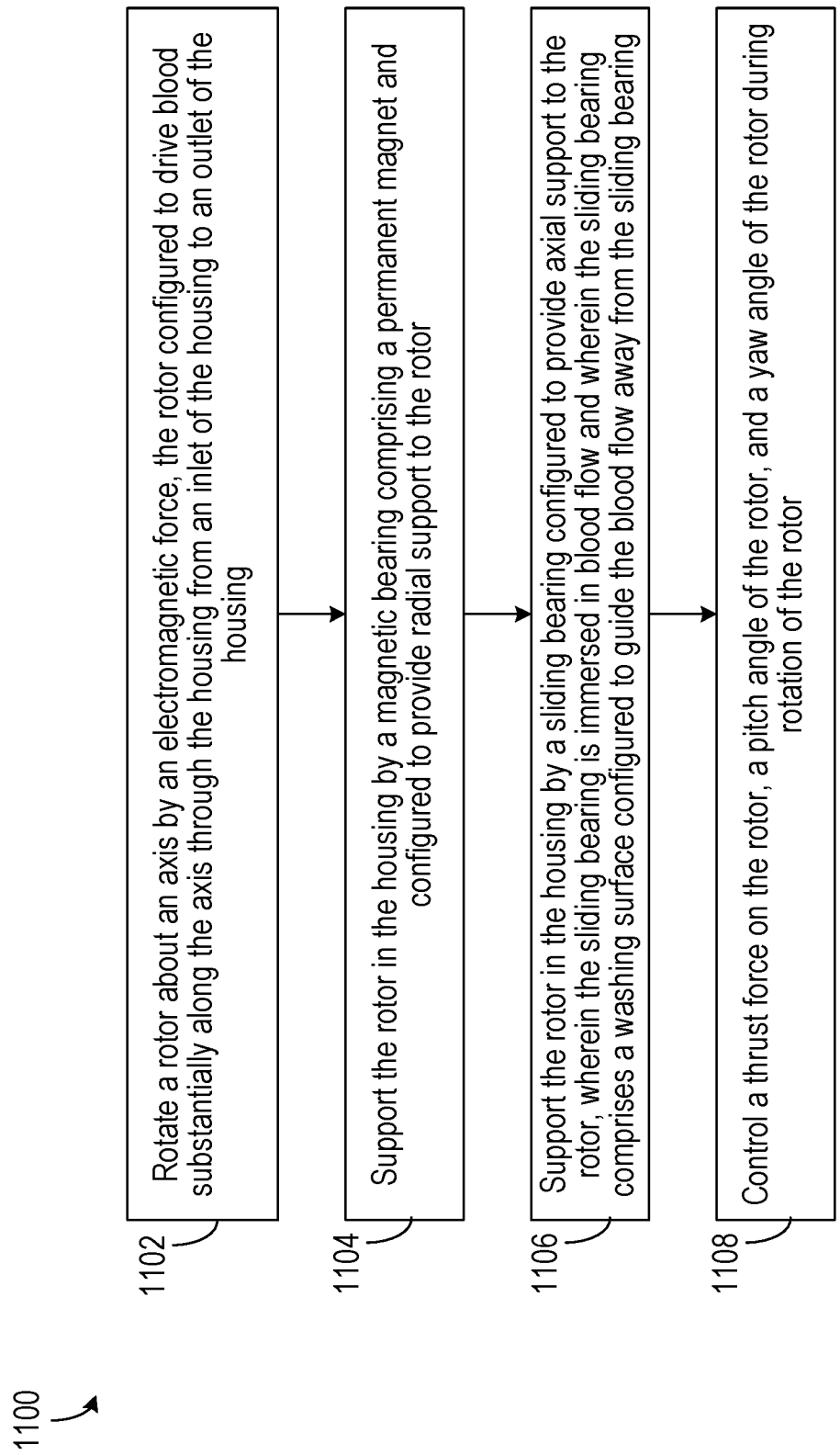

BLOOD-IMMERSED BEARING SYSTEM FOR A BLOOD PUMP

CLAIM OF PRIORITY

This application claims priority under 35 U.S.C. § 119(e) to U.S. Patent Application Ser. No. 62/605,402, filed on Aug. 10, 2017, the entire contents of which are hereby incorporated by reference.

STATEMENT OF GOVERNMENT RIGHTS

This invention was made with government support under grant no. R43-HL077028, Development of a Ventricular Assist System for Toddlers & Small Children, awarded by the National Institutes of Health/NHLBI. The government has certain rights in the invention.

TECHNICAL FIELD

This document relates to blood pumps, and more particularly to blood-immersed bearings for a rotodynamic blood pump.

BACKGROUND

Heart-assist pumps for patients with severe forms of the disease are becoming increasingly common. Because these devices are being used as "destination therapy," the required duration of safe and effective use can be several years.

A common type of heart-assist pump is based on rotodynamic principles and involves a rotating impeller. The rotor is immersed in blood and spins at very high speeds—over 10,000 RPM in some cases.

For many years, developers have struggled to design bearings that will support such rotating impellers that are safe and effective. The most common problems related to trauma of the formed elements (cells) in the blood and specifically to thrombosis, or blood clotting. The consequences are often severe, including stroke, organ damage, pump stoppage, and death. The problem is so acute that some companies have been forced to interrupt clinical trials of new rotodynamic blood pumps due to thrombosis.

The physical and biochemical mechanisms for thrombosis are complex, but primarily relate to the combination of high (shear) stress to the blood and to stagnant or recirculating flow near the bearings that may allow chemical agonists to accumulate.

SUMMARY

The blood pump described herein is configured to pump blood with minimal or zero thrombus (e.g., blood clotting) formation occurring inside the pump, specifically on and near one or more bearings of the blood pump that are configured to be immersed in blood during operation of the blood pump. The one or more bearings that minimize shear stress on blood flowing within the blood pump. The one or more bearings of the blood pump are configured to provide "washing" of otherwise stagnant surfaces by promoting the laminar flow of blood near rotor and stator surfaces of the blood pump and reducing or minimizing turbulent flow near the rotor and the stator surfaces. Because fewer vortices form in the blood pump, particularly near the one more rotor bearings, the risk of thrombus formation in the blood pump decreases.

Rotodynamic (e.g., rotary, turbodynamic, etc.) blood pumps involve rotation of a principally cylindrical (or discoid) rotor. The rotor (e.g., impeller) has physical means of constraint in five degrees of freedom as described in detail below. The five degrees of freedom include pitch, yaw, rectilinear "bounce" (both horizontally and vertically), and axial degrees of freedom. Roll, which is the sixth degree of freedom for the rotor, is provided by the motor to drive the rotor about an axis (extending in the axial direction) and pump blood through the blood pump.

For each of the degrees of freedom, a constraint or support can be provided mechanically (by physical contact), hydrodynamically (by a fluid layer), and/or by non-contact bearings, such as magnetic fields.

The most conventional means of support is by bearings (such as a roller bearing or bushing). However when utilized within blood, there is a risk of blood coagulation or damage due to the combined action of shear stress and friction, causing heating. Therefore, the use of magnetic levitation can used, e.g. as described in U.S. Pat. No. 6,447,266, the contents of which are fully incorporated by reference herein. Magnetic bearings provide the advantages of avoiding physical contact, reducing the amount of shear stress, and reducing the likelihood of thrombosis in the blood pump relative to the likelihood of thrombosis in a blood pump including only mechanical bearings.

In some implementations, magnetic levitation may be provided by permanent magnets and/or electromagnets. However, because it is impossible to completely support a rotor in all degrees of freedom using passive magnets only, it is necessary for at least one degree of freedom to be supported by physical means, or by feedback-controlled electromagnetic means. In some implementations, permanent magnets provide support in the bounce, yaw, and pitch degrees of freedom, and feedback-controlled electromagnets in the axial direction. Such a configuration is a fully-magnetically levitated rotor.

Such fully-magnetically levitated rotors, however, are require extra wires, sensors, and feedback control circuitry, relative to mechanically supported rotors. This document describes a blood pump including a hybrid magnetic/mechanical support system for the rotor of a blood pump that includes a mechanical support means in at least one degree of freedom. The mechanical bearing, also called a sliding bearing, is configured for immersion in blood during operation of the blood pump. The mechanical bearing of the bearing system of the blood pump described herein is therefore configured to minimize thrombus formation in the blood pump.

The mechanical bearing generates a minimal amount of heat during use by including a minimal surface area in which physical contact of the bearing between the rotor and a stator occurs. Example configurations of the mechanical bearing are described in further detail, below.

The mechanical bearing and rotor are designed to reduce vortices and stagnant blood (e.g., "dead spaces" for blood flow) near rotor and stator surfaces inside the blood pump. In other words, the shape of the mechanical bearing, rotor, and stator are designed to promote washing near surfaces of the mechanical bearing, rotor, and stator. Because stagnant blood in the blood pump can induce thrombus formation, the mechanical bearing reduces likelihood of thrombus formation by promoting washing near the mechanical bearing. Here, the term washing refers to areas of non-zero blood flow inside the blood pump. For example, a washing surface or washout channel can increase laminar blood flow near the respective washing surface or washout channel of the mechanical bearing and reduce vortices near the respective surface and/or channel.

A blood pump includes a housing including an inlet and an outlet, an axis of the housing being from the inlet to the outlet. The blood pump includes a rotor disposed in the housing, the rotor configured to rotate substantially about the axis to pump blood from the inlet to the outlet. The axis is a central axis. A stator is disposed within the housing and coupled to the housing. The stator is configured to drive rotation of the rotor about the axis. The blood pump includes a bearing mechanism for supporting the rotor inside the housing, the bearing mechanism including a magnetic bearing and a sliding bearing. The magnetic bearing includes a permanent magnet and is configured to magnetically support the rotor inside the housing in a radial direction from the axis. The magnetic bearing includes a first suspension magnet affixed to the housing and a second suspension magnet affixed to the rotor. The sliding bearing is configured to physically support the rotor inside the housing in an axial direction along the axis of the housing and allow rotation of the rotor substantially about the axis. The sliding bearing includes at least one point of contact where the rotor is configured to physically contact a trunnion affixed to the housing.

In some implementations, the trunnion comprises an arcuate surface configured to contact the rotor and physically support the rotor inside the housing in the axial direction along the axis of the housing and in a radial direction that is substantially orthogonal to the axial direction.

In some implementations, the sliding bearing includes a flat surface of the trunnion configured to contact a tapered point of the rotor and physically support the rotor inside the housing in the axial direction along the axis of the housing.

In some implementations, the trunnion includes a concave surface configured to contact a curved surface of the rotor and physically support the rotor inside the housing in the axial direction along the axis of the housing and in a radial direction that is substantially orthogonal to the axial direction. In some implementations, the trunnion includes a bearing pin extending substantially along the axis, and where the rotor comprises a pointed end configured to contact the bearing pin, where the pointed end of the rotor is configured to align with the axis during rotation of the rotor.

In some implementations, the sliding bearing comprises a plurality of trunnions, and the plurality of trunnions are radially spaced in a blood flow path to allow blood to flow between the trunnions. In some implementations, each trunnion of the plurality of trunnions comprises a convex surface configured to engage the rotor at a respective point of contact, and blood is configured to flow across the convex surface of each trunnion during operation of the blood pump.

In some implementations, the rotor is configured to receive a thrust force in the axial direction when blood is flowing through the housing, and the thrust force is configured to cause the rotor to physically engage the trunnion at the at least one point of contact of the sliding bearing.

In some implementations, the at least one point of contact between the rotor and the trunnion is configured to be submerged in a blood flow path from the inlet to the outlet; and where at least one of the trunnion and the rotor comprises one or more washout passages each configured to direct blood flow away from the at least one point of contact between the rotor and the trunnion.

In some implementations, the sliding bearing is positioned between the inlet of the housing and the magnetic bearing. In some implementations, the sliding bearing is positioned between the outlet of the housing and the magnetic bearing.

In some implementations, at least a portion of the rotor is configured to contact the trunnion comprises a ceramic material.

In some implementations, the sliding bearing is seamless. In some implementations, the trunnion comprises a hollow interior that allows blood to flow within the trunnion and over a contact surface of the trunnion with the rotor. In some implementations, rotor includes an inducer blade that extends from the rotor surface and that is configured to guide blood away from the sliding bearing and towards the outlet of the blood pump.

In some implementations, the bearing mechanism is configured to reduce thrombus formation by at least 25% inside the blood pump. In some implementations, the bearing mechanism is configured to eliminate thrombus formation inside the blood pump.

A method for pumping blood includes rotating a rotor about an axis by an electromagnetic force, the rotor configured to drive blood substantially along the axis through the housing from an inlet of the housing to an outlet of the housing. The method includes supporting the rotor in the housing by a magnetic bearing including a permanent magnet and configured to provide radial support to the rotor. The method includes supporting the rotor in the housing by a sliding bearing configured to provide axial support to the rotor. The sliding bearing is immersed in blood flow. The sliding bearing comprises a washing surface configured to guide the blood flow away from the sliding bearing; controlling, by a controller, a thrust force on the rotor, a pitch angle of the rotor, and a yaw angle of the rotor during rotation of the rotor.

In some implementations, the method includes reducing thrombus formation to in the blood pump by at least 50%. In some implementations, the method includes eliminating thrombus formation in the blood pump. In some implementations, the pressure range of pumping caused by the rotor rotating is between 75-125 mm/Hg.

Although the blood pump described herein is suitable for other uses besides pumping blood, such as food products and petrochemicals in which the operating fluid is susceptible to clotting, it will be described as being used as a blood pump for pumping fluid through a patient. Such description is for purposes of explanation and is not intended to limit the scope of this description The details of one or more embodiments of the blood pump are set forth in the accompanying drawings and the description below. Other features, objects, and advantages of the blood pump will be apparent from the description and drawings, and from the claims.

DESCRIPTION OF DRAWINGS

FIG. 9A shows a side view of an example blood pump including a bearing system.

FIG. 9B shows a close-up side view of a mechanical bearing of the blood pump of FIG. 9A.

FIG. 10A shows a side view of an example blood pump including non-axial outlet.

FIG. 10B shows a close-up side view of a mechanical bearing of the blood pump of FIG. 10A.

FIG. 11 shows a process for pumping blood.

Like reference symbols in the various drawings indicate like elements.

DETAILED DESCRIPTION

Figure 1A:
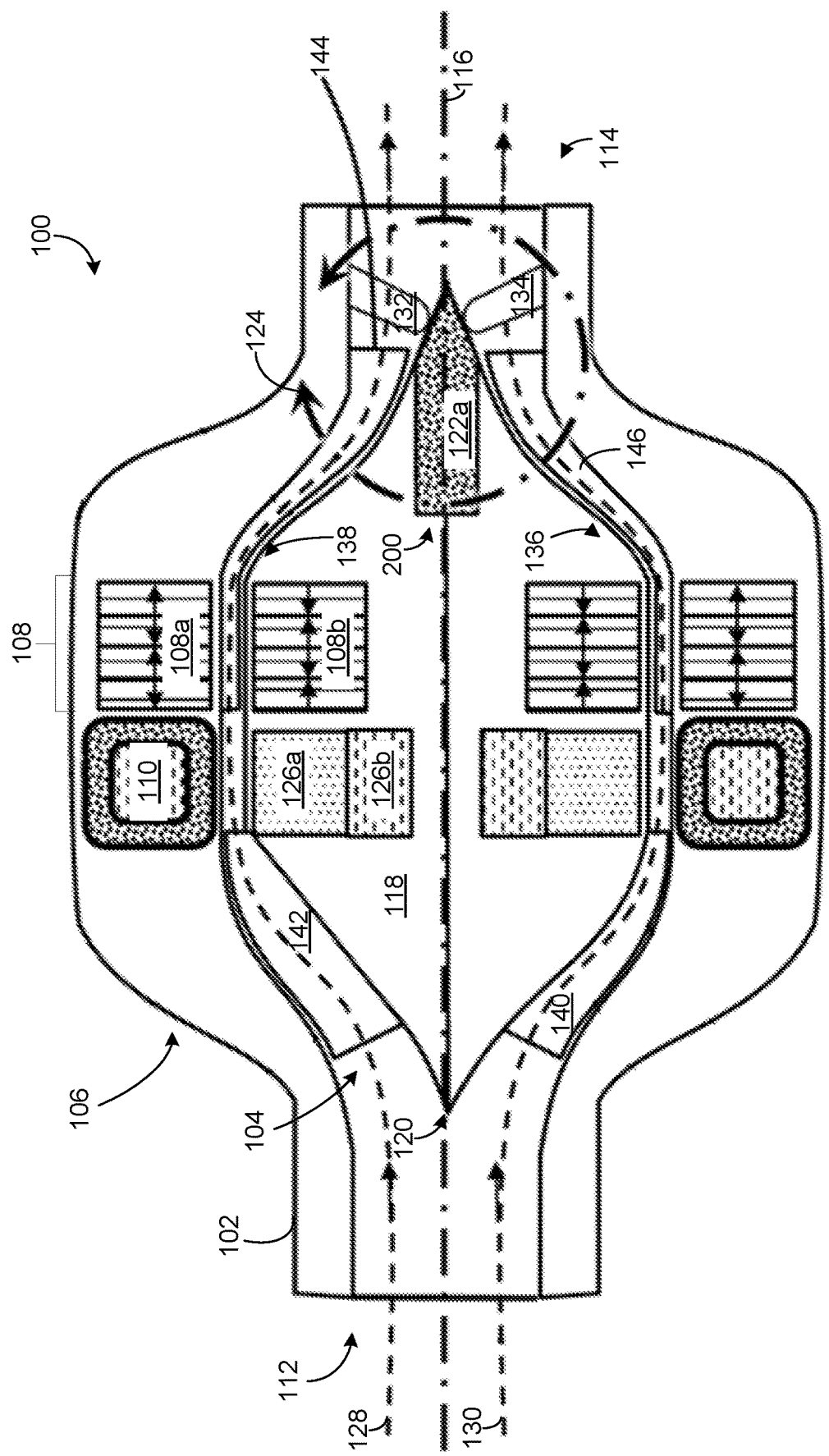
FIGS. 1A-1B show side views of an example blood pump including a bearing system.
Figure 1B:
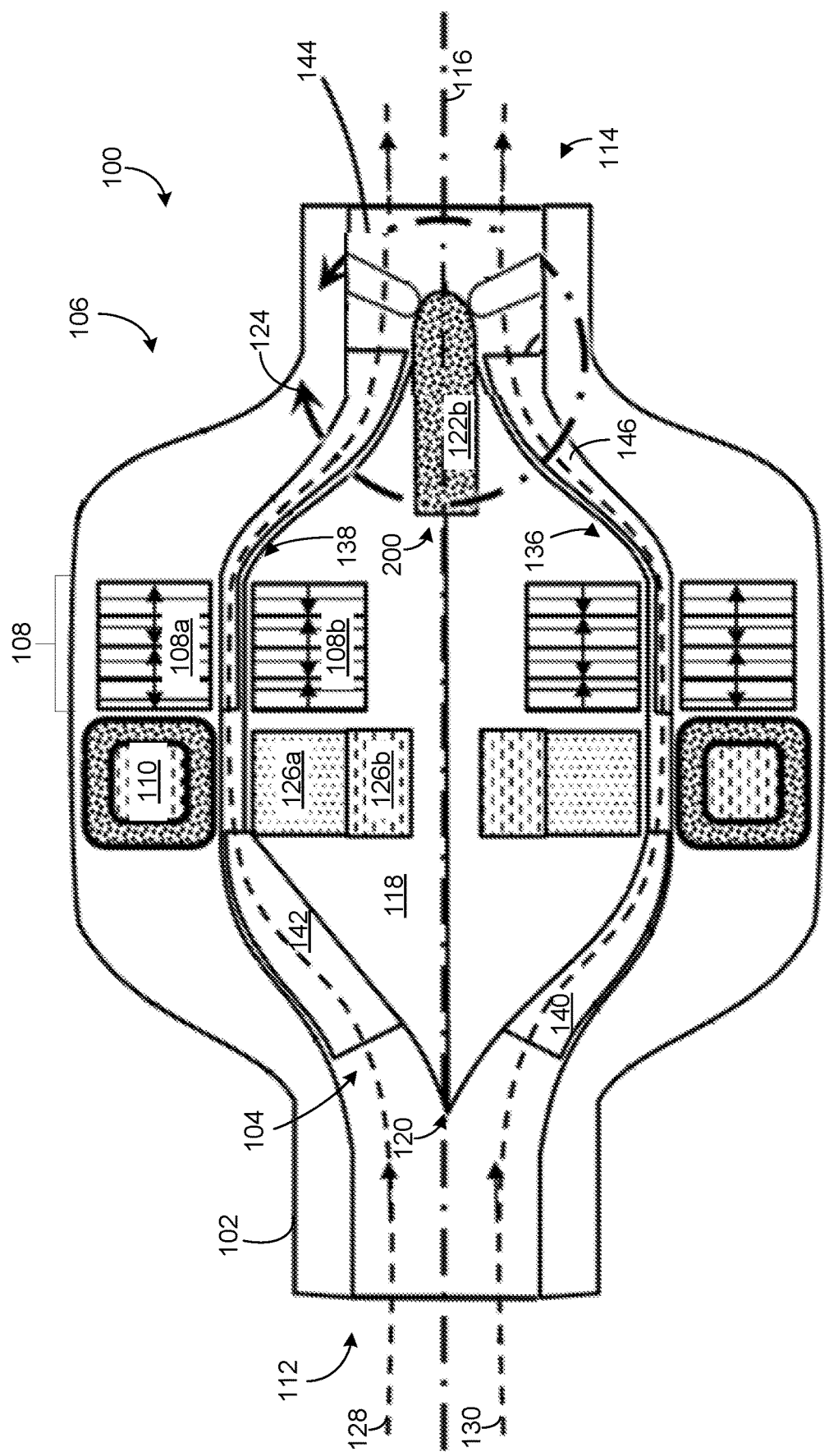

FIGS. 1A-1B show side views of a blood pump 100 including a bearing system. The blood pump 100 is an axial rotary pump having a housing 102, a rotor 104 (e.g., impeller) with impeller blades 140, 142, a stator member 106, magnetic bearing 108 for levitating the rotor 104 within the housing 102 (e.g., at a centered position) and a means for rotating the rotor 104 (e.g., an electromagnetic motor stator 110 that cooperates with rotor magnets 126a and back iron 126b to form an electromagnetic motor). The stator 106 refers to portions of the blood pump 100 that are stator members, such as it is an assembly of a portion of the housing 102, stator blades 144, and trunnions 132, 134.

The housing 102 is substantially cylindrical and has an inlet 112 and an outlet 114. The inlet and the outlet are approximately aligned along an axis 116 about which the rotor is configured to rotate. The housing 102 holds magnetic rings 108a that interact with magnets 108b in the rotor 104 to magnetically support the rotor (at a centered position) in the housing 102 and form the magnetic bearing 108. The magnetic bearing 108 can include permanent magnets to support the rotor 104. The housing 102 is configured to couple with an inlet cannula (tube) and an outlet cannula. Blood flow is configured to enter the blood pump 100 from the inlet 112 to the outlet 114. For example, the blood flow path can be through the housing 102 and around the rotor 104, shown by arrows 128 and 130. Blood flows across mechanical bearing 200 during use of the blood pump 100. Mechanical bearing 200 is thus a blood-immersed bearing.

The rotor 104 has a substantially axially symmetric elongated body 118, a conical-shaped tail 122 and a nose 120. The tail 122 forms a portion of a mechanical bearing 200 (seen in FIGS. 2A-2B and delineated by a dashed circle 124 in FIGS. 1A-1B). The rotor 104 includes portions of the magnetic bearing 108 and of the mechanical bearing 200. For example, the rotor 104 includes magnets 108b (forming a ring) which levitate the rotor 104 within the housing 102. The rotor 104 includes magnets 126a and iron backing 126b. The magnets 126a and backing 126b interact with electromagnets 110, respectively to drive the rotor 104 to rotate substantially about axis 116, as described below. The tail 122 is conical-shaped, such that the end of the tail is tapered in a rotatably symmetric manner. The tail 122 forms a portion of the mechanical bearing 200, and physically contacts a portion of the stator 106 to form a sliding bearing that provides thrust support during operation (e.g., when blood is flowing through the housing from the inlet 112 toward the outlet 114). In the example blood pump 100 of FIGS. 1A-1B, the tail 122 is rounded and the stator 106 includes a plurality of support trunnions (e.g., support pylons, support extensions, etc.). In FIGS. 1A-1B, two trunnions 132, 134, are shown. However, typically, three or more trunnions are included for the mechanical bearing 200. The mechanical bearing 200 is described in detail with respect to FIGS. 2A-2B. The nose 120 and/or the trunnions 132, 134 can be coated with or made from a ceramic material. Such materials may be alumina, zirconia, ruby, diamond, yttrium oxide or any other material having superior hardness and wear resistance, such as high molecular weight polyethylene.

The stator member 106 includes a motor stator 110, portion 108a of magnetic bearing 108, and may include an angle sensor (not shown), such as an encoder. The stator 106 includes a portion of the mechanical bearing 200 that forms a sliding bearing with a portion of the rotor 104 (e.g., tail 122a-b that rotates with the rotor 104). In some implementations, the stator 106 includes a set of stationary blades 144, 146 that are attached to the housing 102 and define a blood flow passageway (e.g., blood flow paths 128, 130). Stator blades 144, 146 extend from the interior of the housing. The stator blades 144, 146 are inwardly directed and spiral. The stator blades 144, 146 are stationary blades and have a gap between tips of the stator blades and the rotor tail 122a-b, serving to "unwind" a spiral blood flow generated by the impeller blades, thereby recovering pressure.

In some implementations, the means for rotating the rotor is a brushless DC motor having a motor stator comprising coil wrapped iron poles 110, an angle sensor (not shown), a rotor elongated body 118 having permanent magnets 126a and iron backing 126b, flux-focusing structures made from a soft magnetic material, and impeller blades 140, 142 on the exterior of the rotor 104. The impeller blades 140, 142 can also serve as the motor poles (e.g., include magnets 126a and iron backing 126b) and are made from a soft magnetic material coated with a biocompatible material. In some implementations, there are two rotor blades, but additional blades can be added in a rotationally symmetric pattern about axis 116. The motor stator 110 and the angle sensor are positioned within the housing 102 between an internal surface and an external surface of the housing that defines the blood flow passage from the inlet 112 to the outlet 114. Motor stator coils are wound on the motor stator 110. Current through the motor stator coil can be controlled to affect the desired speed of the rotor 104. Although this is a particular means for rotating the rotor, a variety of other rotational means can be used in the blood pump. Alternatively, the brushless D.C. motor can take the form of a two pole motor.

The magnetic bearing 108 provides positive radial stiffness and negative axial stiffness. In the preferred embodiment, the magnetic bearing 108 is comprised of two sets of stacked magnetic rings 108a and 108b that are axially magnetized, with alternating polarity to impart a repulsive force. Such a magnetic bearing is commonly known as a Backers bearing, and is described in Paden B E, N J Groom, and J F Antaki. *Design formulae for permanent magnet bearings. ASME J Mechanical Design,* 125:734-738, 2003. In some implementations, position sensors (not shown) are attached to the inlet 112 and the outlet 114 of the housing 102 and adjacent to the rotor tail 122 and the rotor nose 120. Any position sensor can be used including a Hall Effect, eddy-current, or infrared optical sensors. The rotor 104 position can even be sensed from changes in inductances of the coils. Electromagnetic motors controlled with such a sensing scheme are referred to as brushless DC motors. During operation of the blood pump 100, the blood enters the inlet 112 of the housing 102 in the direction of the arrows 128, 130. The blood passes over the rotor nose 120 through the gaps 136, 138. The rotor 104 is rotated by the rotating means 110 and 126a-b. The impeller blades 140, 142 accelerate and impart energy to the blood such that the blood moves through the housing 102 toward the outlet 114 from the inlet 112. The impeller blades 140, 142 can be curved or have other such geometry to drive the fluid (e.g., blood) in the blood pump 100 substantially in an axial direction toward the outlet 114. Before exiting the housing 102, the blood passes through the gaps 136, 138 and the blood flow paths 128, 130. The gaps 136 and 138 are sized and proportioned such that they are large enough to prevent regions of stagnation and excessive shear from forming while being small enough to provide efficient magnetic suspension of the rotor 104. Furthermore, the axially symmetric configuration of the rotor body 118 provides for blood to flow through the housing 102 without creating regions of stagnation or excessive shear force on the blood.

The geometric configurations of the rotor 104 and stator 106 affect the hydrodynamic performance and the biocompatibility of the blood pump 100. Specifically, the flow paths 128, 130 (which form a radial flow path around the rotor 104) is configured to avoid regions of high fluid stress that may damage cells of blood flowing through the blood pump 100 and/or activate the clotting process. Further, the rotor 104 and stator 106 geometry are configured to reduce or eliminate regions of blood stagnation in the blood pump 100 that may result in depositions of blood elements on the blood pump. These depositions (thrombus formation on the rotor 104/stator 106) can cause embolism and possibly stroke. The rotor 104 and stator 106 geometries are configured to form a mechanical bearing 200 (also called a sliding bearing) that provides thrust support for the rotor in a substantially axial direction along axis 116 and that minimizes thrombus formation in the blood pump 100, as described below. The mechanical bearing also provides radial support, and in cooperation with permanent magnet 108 provides moment support, i.e. restricting pitch and yaw of the rotor 104. The terms "minimizing or reducing," in this context are indicative of reducing a value (e.g., of friction or heat) or reducing a prevalence (e.g., of thrombus formation) by at least 10 percent, at least 25 percent, etc., as compared to a control. The phrase "substantially eliminating" a thrombus formation refers to removing all but negligible blood clotting or clot buildup on or near the blood pump interior.

The model for the blood flow is preferably the incompressible Navier-Stokes and conservation of mass equations. Use of the former equations assumes that blood can be treated as a single-phase homogenous linear viscous fluid. In order to solve this equation, a Galerkin finite-element program was written for this purpose. This program uses quadratic velocity-linear pressure elements within a mixed formulation of the steady equations. These element types are known to be stable and produce approximations of optimal order. The resulting, non-linear algebraic system is solved by a Newton continuation method. Analytical gradients of the objective functions are computed using a direct differentiation method.

The objective function used in the above-method represents the desired design criterion to be minimized. For example, the objective functions relating to trauma and platelet activation include, but are not limited to shear stress with respect to resident time, viscous energy dissipation rates, particle acceleration, negative pressure causing outgassing or cavitation, and measurements of turbulence intensities. The objective functions defining stagnation and deposition include but are not limited to vorticity, reverse flow (i.e., boundary layer shear locally becoming zero), adverse pressure gradient, the standard deviation of consecutive blade-to-blade axial velocity, and boundary layer transport. This list is illustrative but is not exhaustive to the objective functions that can be utilized for designing geometric configurations for the blood pump of the present preferred blood pump. These concepts are described further in publications such as A. J. Stepanoff, *Centrifugal and Axial Flow Pumps: Theory, Design, and Application* 2nd Edition, 1993.

Figure 2A:
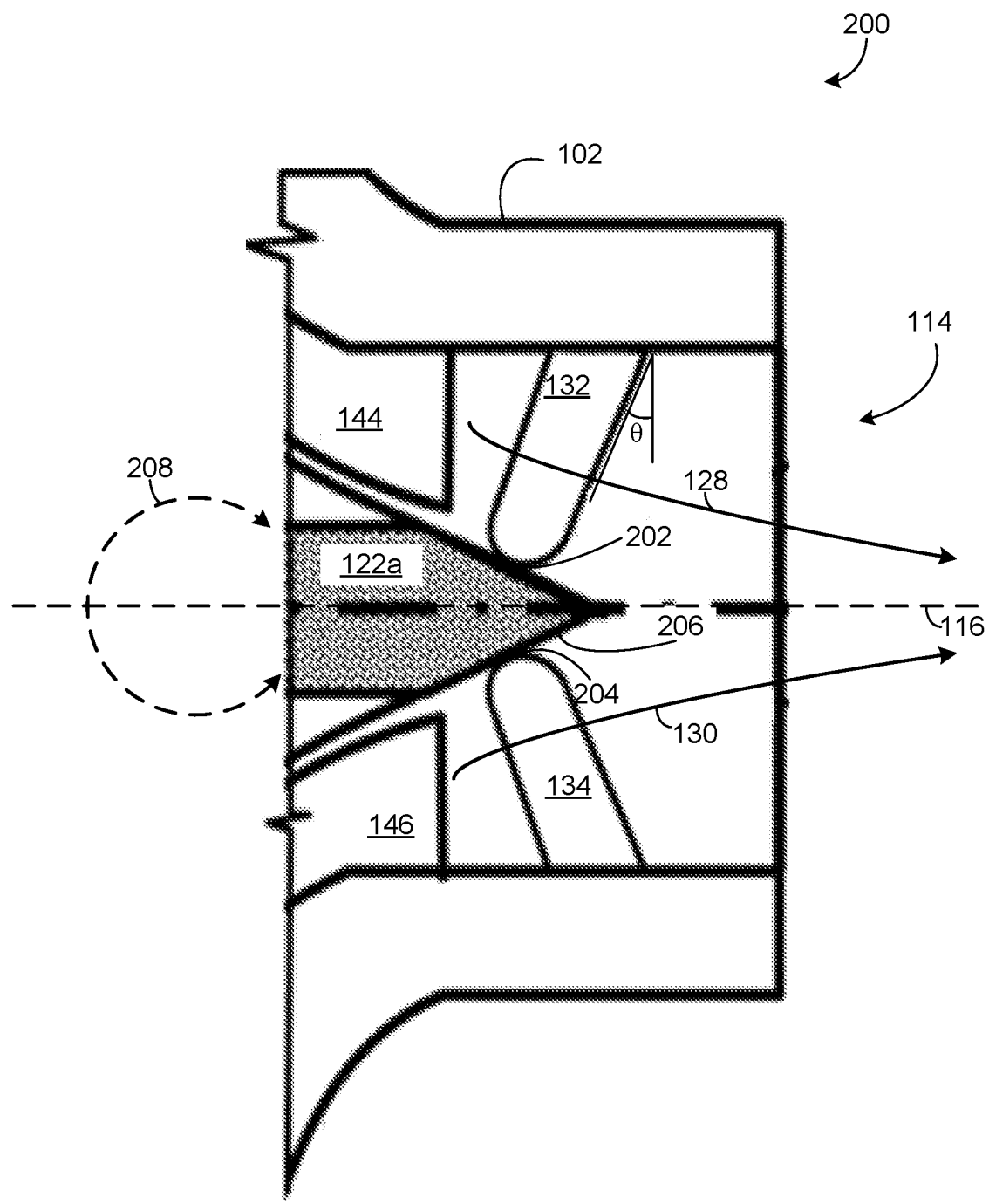
FIGS. 2A-2B show close-up side views of a mechanical bearing of the blood pump of FIGS. 1A-1B, respectively.
Figure 2B:
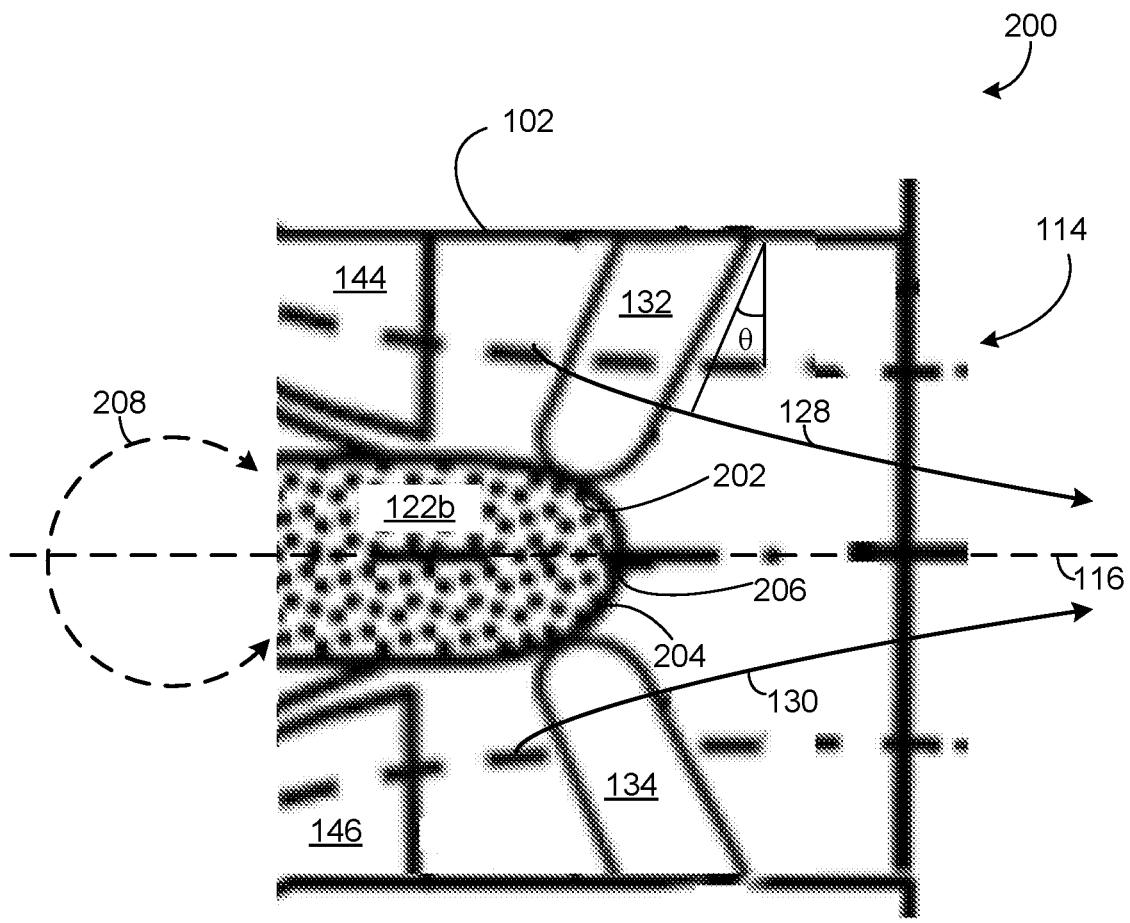

Turning to FIGS. 2A-2B, a close-up side view of a mechanical bearing 200 of the blood pump 100 of FIGS. 1A-1B, respectively, is shown. FIGS. 2A-2B approximately correspond to the portion of the blood pump 100 delineated by border 124 of FIGS. 1A-1B. The mechanical bearing 200 provides support for the rotor 104 in the thrust (axial) direction and prevents the rotor 104 from contacting the housing 102 and/or stator 106 in response to the thrust forces generated by the combined action of the permanent magnet bearing 108 and the pressure rise caused by the rotation of the rotor 104, while allowing the rotor 104 to rotate substantially about axis 104.

The thrust support of the mechanical bearing 200 stabilizes the rotor 104 based on the forces of blood flowing over the mechanical bearing 200 and based on thrust support provided by magnetic bearing 108. When fluid (e.g., blood) is flowing through the blood pump 100, it provides a thrust force on the rotor 104 in the axial direction from the outlet 114 towards the inlet 112 as the rotor pumps the fluid from the inlet toward the outlet. The magnetic bearing 108 provides thrust support to the rotor 104 in response to forces from the blood that pull the rotor 104 toward the inlet 112. The magnetic bearing 108 provides a bias force on the rotor 104 in the axial direction 116 toward the outlet 114. The mechanical bearing 200 stabilizes the rotor 104 and keeps the bias force in equilibrium during operation of the blood pump 100.

The positioning of the mechanical bearing 200 at the tail of the rotor 104 is advantageous since the pressure force caused by the rotation of the rotor 104 will negate the magnetic force imparted by the magnetic bearing 108, and thereby reduce friction, heat, and thus thrombus formation in the blood pump. The pressure of the blood pump 100 is approximately 100 mm/Hg, but can vary between 75-125 mm/Hg. In some implementations, the blood pump pressure is similar to pressures conventional for blood pump operation.

The mechanical bearing 200 includes the tail 122 of the rotor 104. The tail 122 of the rotor 104 includes a surface 206 that forms a portion of the mechanical bearing 200. The surface 206 is a rounded surface. In some implementations, the surface 206 is rotationally symmetric about axis 116. For example, surface 206 can be a conical surface. The tail 122 of the rotor 104 can be rounded (e.g., as shown by tail 122b in FIG. 1B). For example, a cross-section of the tail 122 of the rotor 104 can include a substantially parabolic profile. In some implementations, the profile of the tail 122 need not be parabolic, but simply arcuate such that rotational symmetry is maintained. In some implementations, the profile of the tail 122 can be circular. In some implementations, the profile of the tail 122 can be triangular (e.g., as seen by tail 122a in FIG. 1A).

The surface 206 of the tail 122 of the rotor is configured to contact a plurality of trunnions (e.g., trunnions 132, 134) that are affixed to the stator 106 and/or a portion of the housing 102. In the preferred implementations, three trunnions are used, though the side view of FIGS. 2A-2B shows two trunnions, trunnion 132 and trunnion 134. The plurality of trunnions are configured to provide axial support to the rotor in a thrust direction along axis 116, and in cooperation with permanent magnet 108 provides moment support, i.e. restricting pitch and yaw of the rotor 104. Each of the trunnions 132, 134 extends from the housing 102 near the inlet 112. In some implementations, each trunnion 132, 134 forms an angle θ, marked in FIGS. 2A-2B, with an axis that is normal to the housing 102. The angle θ can be adjusted to minimize the contact surface of the trunnions 132, 134 with the surface 206 of the nose 120. In the preferred embodiment, the trunnions are provided at an angle of approximately 45 degrees to provide both thrust and radial vector. However, the angle of the trunnions can vary +/−10%. Each of the trunnions 132, 134 have curved surfaces 202, 204, respectively. Surfaces 202, 204 are configured to contact the surface 206 of the nose 120. Although surfaces 202, 204 appear to be arced edges, a three-dimensional perspective shows that each surface 202, 204 is a curved surface rather than an edge. Surface 206, which is also curved as described above, slides across trunnions 132, 134 while rotating to form a sliding bearing 200. Because each of the surfaces 202, 204, 206 is curved, there is minimal contact (e.g., less than 5% of the trunnion surface) between each of the surfaces 202, 206 and 204, 206 (in addition to additional, similarly situated trunnions that are not pictured in FIGS. 2A-2B).

The trunnions of the plurality can be symmetrically spaced in a radial configuration on the housing 102 near the outlet 114 (e.g., of FIGS. 1A, 1B) so that each trunnion imparts a symmetric force on the tail 122 of the rotor 104. The trunnions provide axial support and radial support to the rotor 104. For example, the trunnions support the tail 122 of the rotor 104 so that the nose is substantially aligned with the axis 116. Radial support ensures that the rotor 104 rotates substantially around axis 116 (e.g., the axis of rotation of the rotor does not deviate more than 5 degrees from axis 116) and efficiently drives the fluid from the inlet 112 toward the outlet 114. For example, the trunnions prevent the rotor 104 from tilting in a pitch direction and a yaw direction such that the nose 120 misaligns with the axis 116. For example, the trunnions prevent the rotor from tilting in a pitch direction and a yaw direction (e.g., with respect to the axis 116) more than 5 degrees as a transient response to forces during operation, and keep the rotor 104 axis aligned with axis 116 (e.g., less than 2 degrees deviation) as a steady-state response. The magnetic bearing 108, described above, also provides radial support, working in concert with the mechanical bearing 200 to stabilize the rotor 104 in the radial (e.g., pitch and yaw) directions with respect to axis 116.

In some implementations, at least three trunnions are used in the mechanical bearing 200, including trunnions 132, 134. In some implementations, four, five, six, or more trunnions can be used. The number of trunnions is restricted by the amount of space between the trunnions. As blood flows between the trunnions, there should be sufficient space so that stagnant flow areas are avoided so that thrombus formation is minimized. In some implementations, the preferred number of trunnions is three, which maximizes the space between the trunnions while providing axial and radial stability for the rotor 104 and approximately equalizes force distribution on the trunnions. As described above, each of the trunnions includes a substantially similar geometry to the other trunnions. The plurality of trunnions are symmetrically configured to support the rotor 104. The rotor 104 is supported in the pitch and yaw directions relative to the axis 116 by the magnetic bearing 108 and mechanical bearing 200 combination. However, the magnetic bearing 108 and mechanical bearing 200 allow the rotor 104 to pitch and yaw without moving axially. This reduces the stiffness requirement of the magnetic bearing 108 and manufacturing precision requirements (e.g., increases error tolerances of manufacturing) and improves the reliability/robustness of performance of the blood pump 100.

When fluid (e.g., blood) is flowing through the blood pump 100, the mechanical bearing 200 is immersed. The blood flows over the mechanical bearing 200, shown by flow arrows 128, 130. The blood flows over the mechanical bearing 200 at the points where the trunnions 132, 134 contact the tail 122 of the rotor 104. As the rotor 104 rotates (e.g., as shown by arrow 208), the nose slides across the trunnions. The sliding contact creates a shear force on the blood flowing over the contact points and heats the contact points (e.g., due to friction). The heat and shear force are minimized by minimizing the contact points of the mechanical bearing 200 and positioning the contact points as closely to the central axis 116 as possible. In the preferred embodiment, the radial distance of the contact points from the central axis is 2 mm. The mechanical bearing 200 has a minimal contact area for each trunnion (less than 5% of the surface area), which can be a point of contact. This reduces the amount of blood that is exposed to elevated shear stress, which could damage blood cells or activate platelets causing thrombosis. This also minimizes the friction (and thus the heat) created by the mechanical bearing 200, reducing and/or eliminating thrombus formation on/near the mechanical bearing, relative to a conventional ball-and-socket or cone-and-cone bearing. The mechanical bearing 200 heats the blood less than 4° C. The contact points between the nose 120 and the trunnions 132, 134 are openly exposed to the flow path of the blood through the blood pump 100. The exposure of the contact points enables blood to wash over each of the surfaces during operation of the blood pump 100. Crevices or blind regions within the blood flow path are minimized such that blood does not stagnate within or near the mechanical bearing 200. Rather, blood is continually pulled across the mechanical bearing 200. The blood flow carries heat away from the mechanical bearing 200. The configuration of the mechanical bearing 200 ensures that a particular portion of the blood is not heated above a threshold (e.g., 4° C.) which may induce denaturation of plasma proteins, damage to blood cells, and/or thrombus formation on/near the mechanical bearing 200. The mechanical bearing is seamless such that blood cannot be trapped between the rotor 104 and the stator 106 or the housing 102. This is different from a conventional ball-and-socket bearing configuration, which includes an exterior bearing seam between the rotating rotor and the stator that are coupled by the ball bearing. The rotor 104 can thus include a monolithic or approximately monolithic exterior, where the outer surface is continuous and seamless such that blood is not trapped in seams or on the surface of the rotor 104 to induce thrombosis. The tapered nose 120 guides blood to flow over the rotor 104 toward the impeller blades 140, 142 and toward the outlet 114. In some implementations, grooves (not shown) can be cut into the nose 120 to further guide blood to flow to the blades 140, 142 and serve as washout passages away from the points of contact of the nose with the trunnions. In some implementations, an induction blade (not shown) can be affixed the nose 120 to further guide blood to flow to the blades 140, 142 and serve as a washout passage away from the points of contact of the nose with the trunnions 132, 134.

Additionally, the trunnions 132, 134 are configured to contact the nose 120 within 2 mm of the leading edge of the nose (e.g., referring to a longitudinal direction, rather than the radial direction/separation referenced above). The trunnions 132, 134 are configured to contact the nose 120 close to the axis 116 of rotation of the rotor 104 and the nose 120 to reduce a radius of contact of the rotor at the point of contact, relative to a larger radius of contact of the rotor distant from the front edge of the nose 120 and far from the axis 116 of rotation. Minimizing the radius of contact in this way reduces the linear velocity (e.g., under 200 cm/s) of the rotor 104 at the point of contact of the mechanical bearing 200, reducing friction and shear forces on blood flowing over the mechanical bearing.

The mechanical bearing 200 of FIGS. 2A-2B is one particular example of a possible mechanical bearing of the bearing system of the blood pump 100. Other examples are described in detail, below. The examples described below (and other designs that minimize shear force and heat generation as described above) can be combined with the blood pump 100, similarly to the mechanical bearing 200.

The mechanical bearing 200 can be near the inlet 112 or near the outlet 114 of the blood pump 100, described in FIGS. 1A-1B. While the embodiment including the mechanical bearing 200 near the outlet 114 is described in detail, an embodiment including the mechanical bearing 200 near the inlet 112 functions in a similar manner with several differences. The mechanical design of the blood pump 100 is approximately the same when the mechanical bearing 200 is near the inlet 114 as when the mechanical bearing 200 is near the outlet 114 (See, e.g., FIGS. 9A-9B, below). The mechanical bearing 200 supports the rotor 104 in the axial direction in response to forces of the blood on the rotor in addition to the thrust imparted by the permanent magnet bearing 118.

Figure 3:
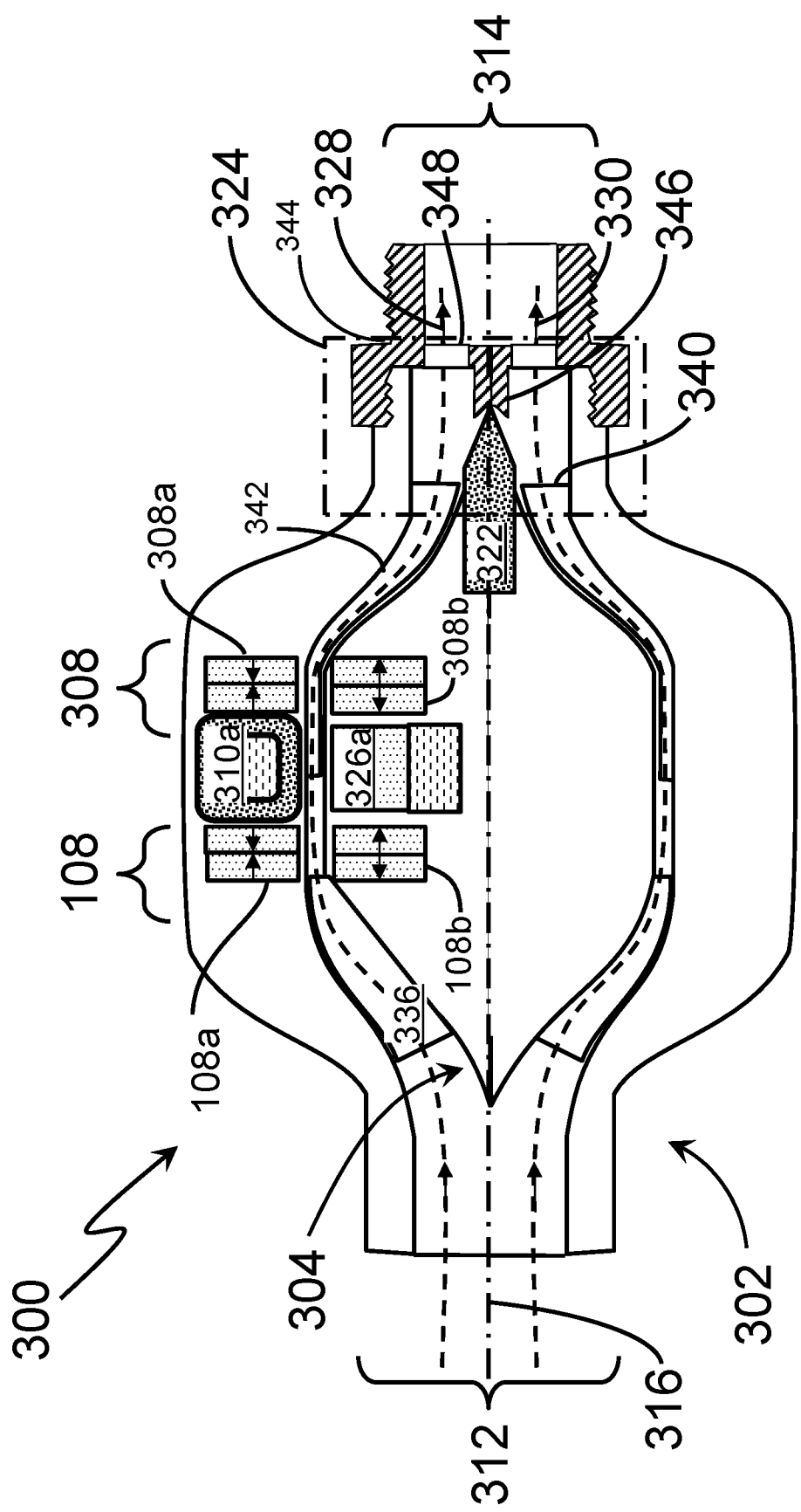
FIG. 3 shows a side view of an example blood pump including a bearing system.

FIG. 3 shows a side view of an example blood pump 300 including a bearing system. The blood pump 300 is similar to blood pump 100 of FIGS. 1A-1B. For purposes of brevity, only the differences between the two blood pumps 100, 300 are described.

The blood pump 300 substantially comprises a housing 302, a rotor 304 positioned within the housing 302, a stator member 306; an inlet 312 and an outlet 314, a magnetic bearing for levitating the rotor 304 within the housing 302, and motor 310 for rotating the rotor 304 using magnets 326a, 326b, similar to the magnets 126a-b that interact with electromagnets 110, as described above in relation to FIGS. 1A-1B. susceptibility. Similar to blood pump 100, the rotor can include rotor blades. The rotor blades can be added in a rotationally symmetric pattern about axis 316, substantially about which rotor 304 rotates. Similar to blood pump 100, stator blades (340, 342) are affixed to the stator and unwind blood flow, recovering flow pressure.

An inflow cannula (not shown) can be attached to the inlet 312 of the housing 304 and an outflow cannula (not shown) can be attached to the outlet 314 of the housing 304. The inflow cannula is a conduit with a first end and a second end. The first end is attached to the housing inlet 312 and the second end is capable of being attached to the left ventricle of a heart. The second end has a trumpet mouth inlet nozzle with an hourglass exterior configuration. Preferably, the inner diameter of the nozzle tapers from twenty millimeters (20 mm) to a final conduit diameter of twelve millimeters (12 mm). Although both the inflow cannula and the outflow cannula can be integrated into the housing of the blood pump 300, it is also possible to have cannula employing quick-connecting mechanisms in such that the rotary pump can be quickly detached from the patient. Examples of cannula are described in Antaki J F, T J Dennis, H Konishi, M E Brown, T R Maher, J P Tomczak, J P Kerrigan, R L Kormos. *An improved left ventricular cannula for chronic dynamic blood pump support. Artificial Organs*, 19(7):671-675, 1995, incorporated herein in entirety by reference.

The stator member 304, the means for rotating the rotor with motor stator 310 and 326a, 326b, and the magnetic bearing 108 for levitating the rotor function substantially the same as those described in FIGS. 1A-1B.

In addition to the magnetic bearing 108 included in the blood pump 300, a second magnetic bearing 308 can be included in the blood pump. The second magnetic bearing 308 comprises similarly permanent magnet stacks 308a, 308b to magnet stacks 108a-b, respectively. The positioning of bearing 308 and bearing 108 on opposite sides of the motor stator 310 and motor magnet 326 serves to increase the pitch and yaw stability with respect to axis 316, about which rotor 304 is configured to rotate as compared to the single configuration in pump 100. The second magnetic bearing 308 also provides additional radial stability to the rotor 304, and the same or greater manufacturing tolerances for the rotor 304 are permissible, similar to rotor 104 of blood pump 100. Fluid (e.g., blood) is configured to pass along paths 328, 330 and through gaps 336, 338 (which form a radial gap between the rotor 304 and the stator 306 and housing 302) from the inlet 312 to the outlet 314.

Blood pump 300 includes a mechanical bearing 400, approximately delineated by box 324 in FIG. 3. The tail 322 is conical, similar to tail 122. Tail 322 has a pointed forward edge (e.g., rather than a rounded forward edge of tail 122b). The pointed forward edge, described in detail with respect to FIG. 4, below, is axially supported by a pin 346. The pin 346 extends along axis 316 and is supported by an extension 344 of the housing 302 that is affixed on the inlet of the housing to create inlet 312. The pin 346 is rigidly affixed to members 348 that radially extend from the pin to the extension 344 to support the pin coaxial with the centerline axis 316. The members 348 are spaced to allow blood flow through gaps between the members 348 with minimal disturbance to the flow of the incoming blood. In some implementations, the members 348 comprise thin blades or airfoils and form a negligible percentage (e.g., <10%) of the cross section of the outlet 314.

Figure 4:
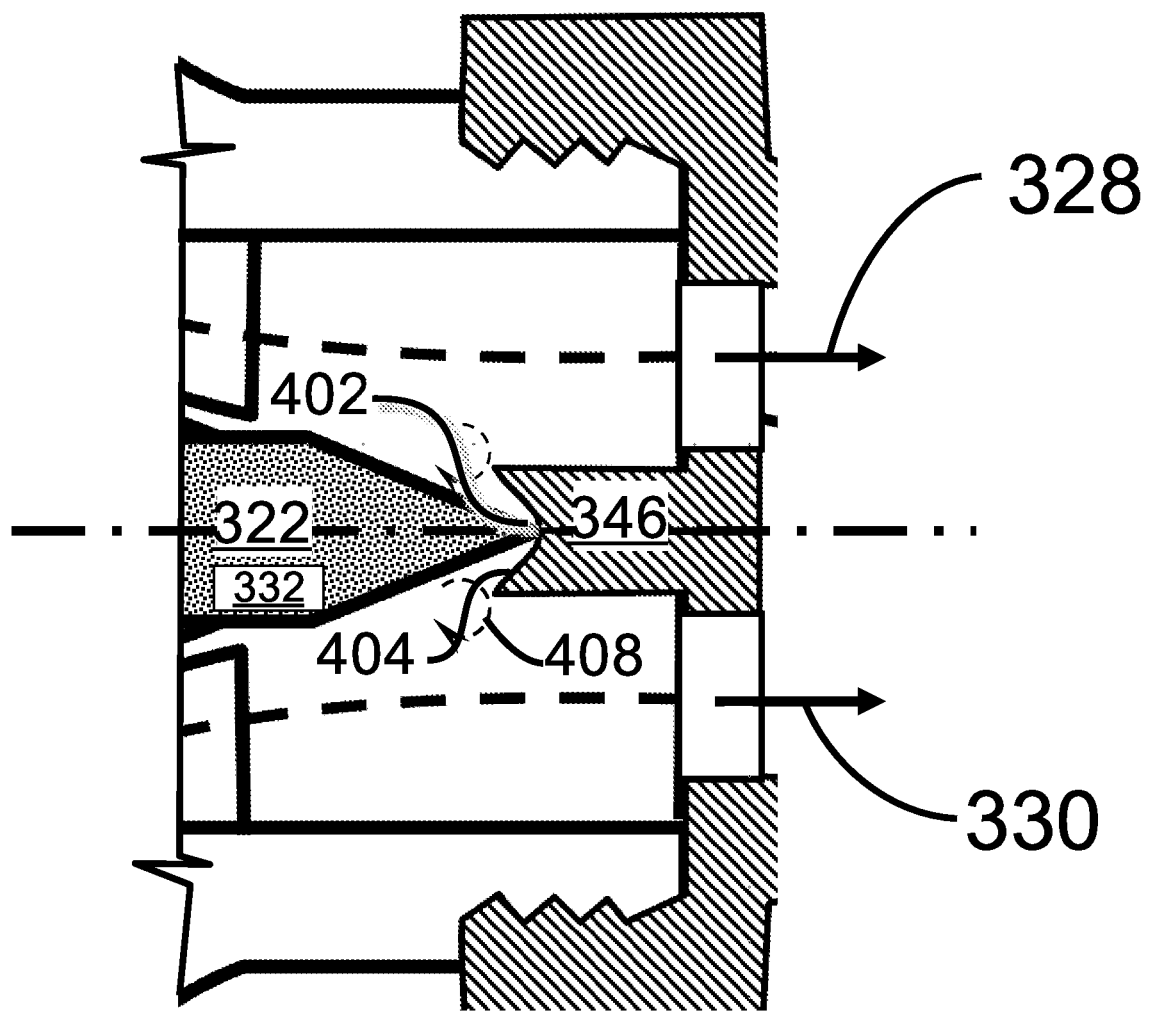
FIG. 4 shows a close-up side view of a mechanical bearing of the blood pump of FIG. 3.

FIG. 4 shows a close-up side view of the mechanical bearing 400 of the blood pump 300 of FIG. 3. The tail 322 of mechanical bearing 400 is conical and tapers to a point 402 that contacts the pin 346 at a pin surface 404. The pin 346 extends substantially along axis 316. As the rotor 304 rotates, the thrust force of the fluid flow on the rotor 304 pushes the tail 322 into the pin 346 at point 402. The point 402 is approximately aligned with axis 316, but is permitted to tilt slightly (e.g., less than 5 degrees) radially from the axis 316, similar to the tail 122 of rotor 104 on the trunnions 132, 124, described in relation to FIGS. 1A-1B. The mechanical bearing 400 enables greater manufacturing tolerances for the dimensions of the rotor 304 when compared to conventional rotors including ball-and-socket or cone-and-cone bearings, because conventional rotors must be machined to a precise dimension that fits into its corresponding housing.

The pin surface 404 is shown as curved (e.g., conical) in FIG. 4. The surface 404 can be concave such that the surface 404 guides the tail 322 leading edge 402 towards the center of the pin 346. Because the center of the pin 346 is axially aligned with the axis 316 about which the rotor rotates, the surface 402 guides the tail 322 to align the axis of the rotor with the center of the blood flow path and the housing 302 axis. In some implementations, surface 404 includes a flat surface without curvature. Mechanical bearing 400 provides primarily axial support on the rotor 304, and relies on the magnetic bearings 108, 308 to provide radial support to the rotor 304. In some implementations, each of the pin 346 and the tail 322 include a ceramic material. For example, each of the pin 346 and the tail 322 can be coated in a ceramic material or be formed from a ceramic material.

The tail 322 contacts the surface 404 of the pin 346 at point 402, which is on the axis of rotation of the rotor 304. The rotor 304 thus contacts the pin 346 with minimal (approximately 0 cm/s) linear velocity, even when the rotor 304 is rotating and driving blood flow. The minimized linear velocity at the contact point 402 of the mechanical bearing 400 reduces friction and thus heat generation, relative to a mechanical bearing requiring a higher contact velocity. The reduced friction and heat generation reduces shear forces on the blood flowing through the mechanical bearing 400 and reduces thrombus formation, relative to a mechanical bearing requiring higher contact velocities (e.g., a ball bearing). Mechanical bearing 400 is seamless and provides minimal areas for stagnant blood flow. Approximate blood flow is shown by arrows 330, 328. Blood is drawn from the inlet and over the mechanical bearing 400. An inducer blade 332 on tail 322 can further draw the blood away from the contact point 402. Vortices 408 are minimized or eliminated as blood is pulled over the mechanical bearing 400. As described below, other bearing designs can be combined into blood pump 300 that replace mechanical bearing 400.

The mechanical bearing 400 can be near the inlet 312 or near the outlet 314 of the blood pump 300, described in FIG. 3. While the embodiment including the mechanical bearing 400 near the inlet is described in detail, an embodiment including the mechanical bearing 400 near the outlet 314 functions in a similar manner with several differences. The thrust support of the mechanical bearing 400 stabilizes the rotor 304 based on the forces of blood flowing over the mechanical bearing 400 and based on thrust support provided by magnetic bearings 108, 308. The magnetic bearings 108, 308 provide thrust support to the rotor 304 in response to forces from the blood that pull the rotor 304 toward the inlet 312. The magnetic bearings 108, 308 provide a bias force on the rotor 304 in the axial direction 316 toward the outlet 314. The mechanical bearing 400 stabilizes the rotor 304 and keeps the bias force in equilibrium during operation of the blood pump 300. The mechanical design of the blood pump 300 is approximately the same when the mechanical bearing 400 is near the outlet 314 as when the mechanical bearing 400 is near the inlet 312. Thus, this blood pump appears to be the same as shown in FIG. 3, but rather the force due to pressure rise caused by the rotation of the impeller would be additive rather than subtractive of the bias force imparted by the magnetic bearing.

Figure 5:
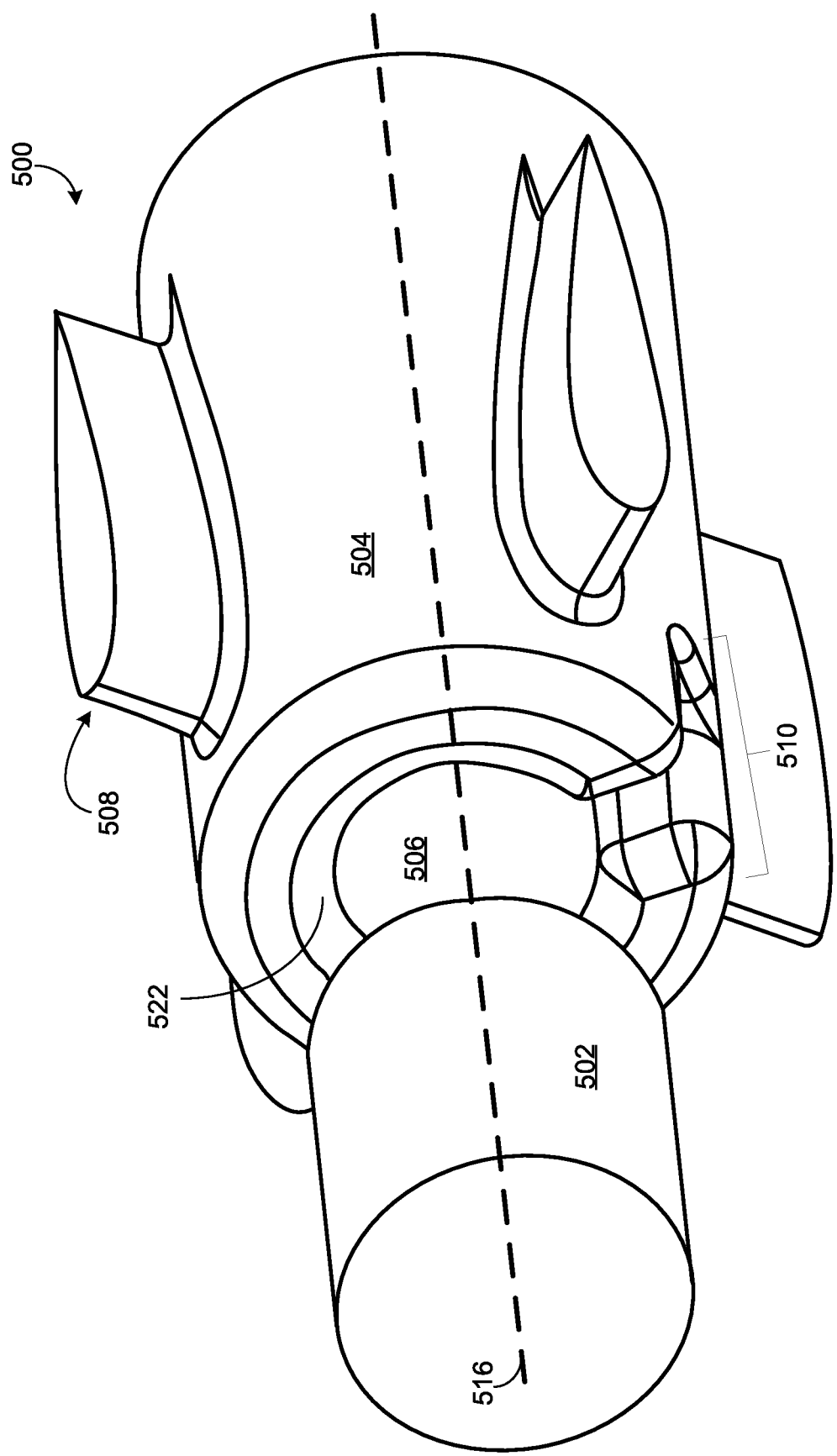
FIG. 5 shows a perspective view of a mechanical bearing for a blood pump.
Figure 6:
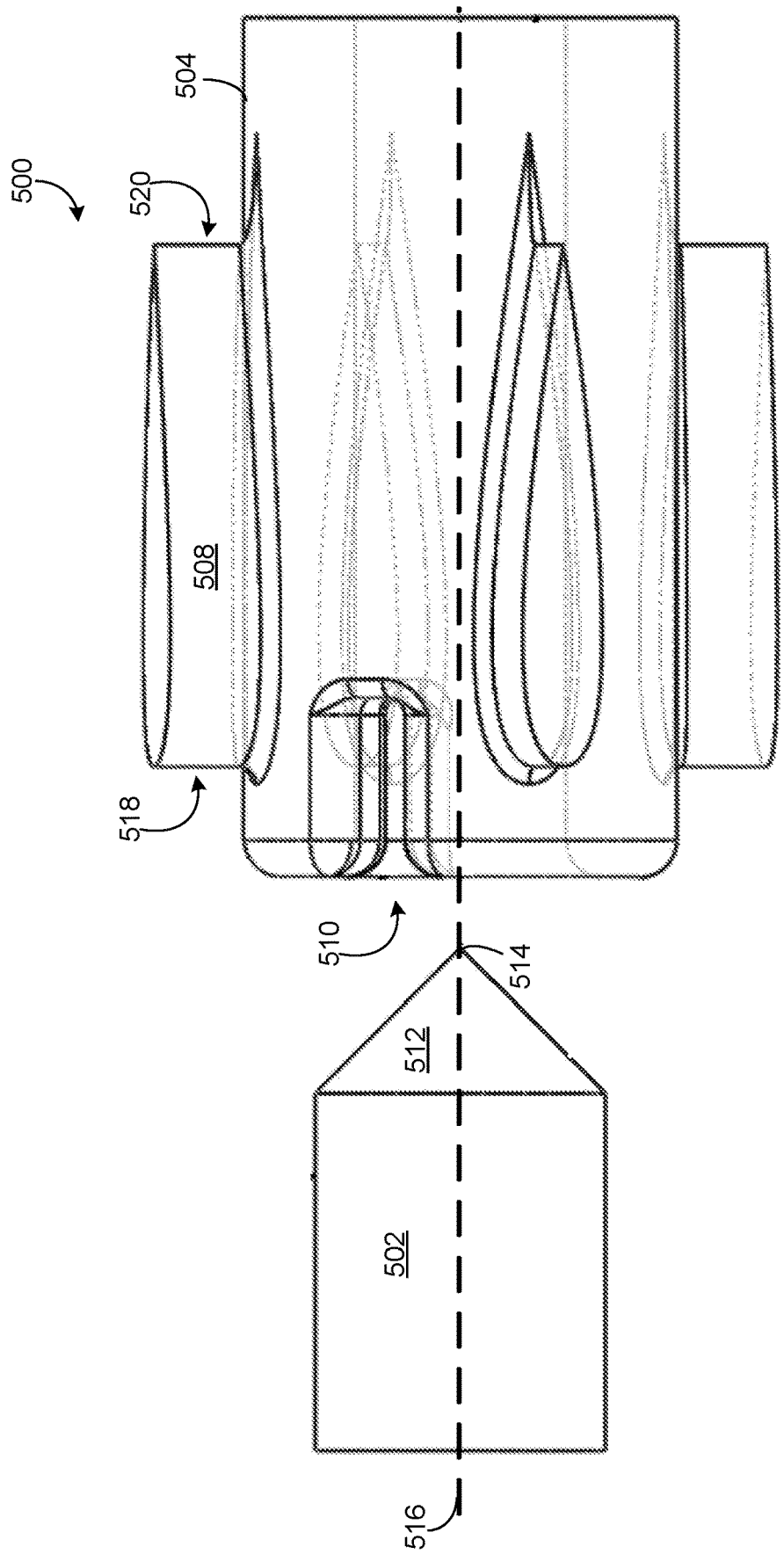
FIG. 6 shows a side-view of the mechanical bearing of FIG. 5.

FIGS. 5-6 show a perspective view and a side view, respectively, of an alternative mechanical bearing 500 for a blood pump (e.g., blood pump 100 of FIGS. 1A-1B or blood pump 300 of FIG. 3). Bearing pin 502 is affixed to a rotor (e.g., rotor 104 or 304) and is configured to couple with a bearing cup 504 (also referred to as a trunnion). The bearing cup 504 is affixed to a housing or other non-rotating portion of a blood pump. Bearing pin 502 is configured to rotate (e.g., about axis 516) and cup 504 is stationary relative to the bearing pin 502 to form a sliding bearing. The mechanical bearing 500 is immersed in blood flow during operation of the blood pump. Blood flow can occur in either direction substantially along axis 516, depending on the configuration of the blood pump. For example, if mechanical bearing 500 is near an inlet of the blood pump, blood flow is a first direction substantially along axis 516 from the bearing cup 504 to the bearing pin 502. For example, if mechanical bearing 500 is near an outlet of the blood pump, blood flow is a second direction substantially along axis 516 from the bearing pin 502 to the bearing cup 504. Blood flow deviates from the axial direction in local areas, but overall flows along axis 516 (as is the case for blood flow in blood pumps 100, 300 and axes 116, 316, respectively). In some implementations, each of the cup 504 and the bearing pin 502 include a ceramic material. For example, each of the cup 504 and the bearing pin 502 can be coated in a layer of ceramic material or be formed entirely from a ceramic material.

The bearing pin 502 includes a rotationally symmetric leading edge 512 that tapers to a point 514. In some implementations, the leading edge 512 is conical. The point 514 is aligned with a rotational axis 516 of the rotor such that the bearing pin 502 is rotatably symmetric about axis 516 and a linear velocity at the point of contact between the bearing pin 502 and the cup 504 is nearly zero cm/s. As described above, a lower linear velocity at the point of contact of the mechanical bearing 500 reduces heat and shear forces on the blood flowing over the mechanical bearing, reducing thrombosis.

The bearing cup 504 includes an inner surface 506 that receives the nose surface 512. In some implementations, the inner surface 506 is flat and receives the point 514 of bearing pin 502. In some implementations, the inner surface 506 is curved and receives a portion of surface 512. For example, the cup 504 can be hollow to allow blood flow over the bearing pin 502 through the cup 504. The cup 504 then supports bearing pin 502 by an axial aperture 522 that contacts surface 512.

In some implementations, the bearing cup 504 includes at least one washout passage 510. The washout passage 510 guides blood flow away from the contact point of the mechanical bearing 500 and reduces stagnation of blood flow around the mechanical bearing. For example, blood that is heated or that experiences shear forces near surface 512 is guided toward blood flow that has occurred away from the mechanical bearing 500, mixing the heated or torn blood cells with cooler blood further from the surface 512. In some implementations, a single washout passage 510 is included. In some implementations, a plurality of washout passages are included.

The cup 504 includes one or more blades 508 extending radially from the cup with respect to axis 516. The blades 508 affix the cup 504 to the housing of the blood pump or other non-rotating portion of the blood pump. Blood flows between the blades 508, which obstruct a negligible percentage (e.g., <10%) of the cross section of the blood flow path. In some implementations, to promote laminar flow through the blades 508, the blades are tapered at edges 518, 520, resembling an airfoil. The number of blades 508 can include two blades, three, four, five, etc. to keep the cup 504 stable in the blood flow path.

Figure 7:
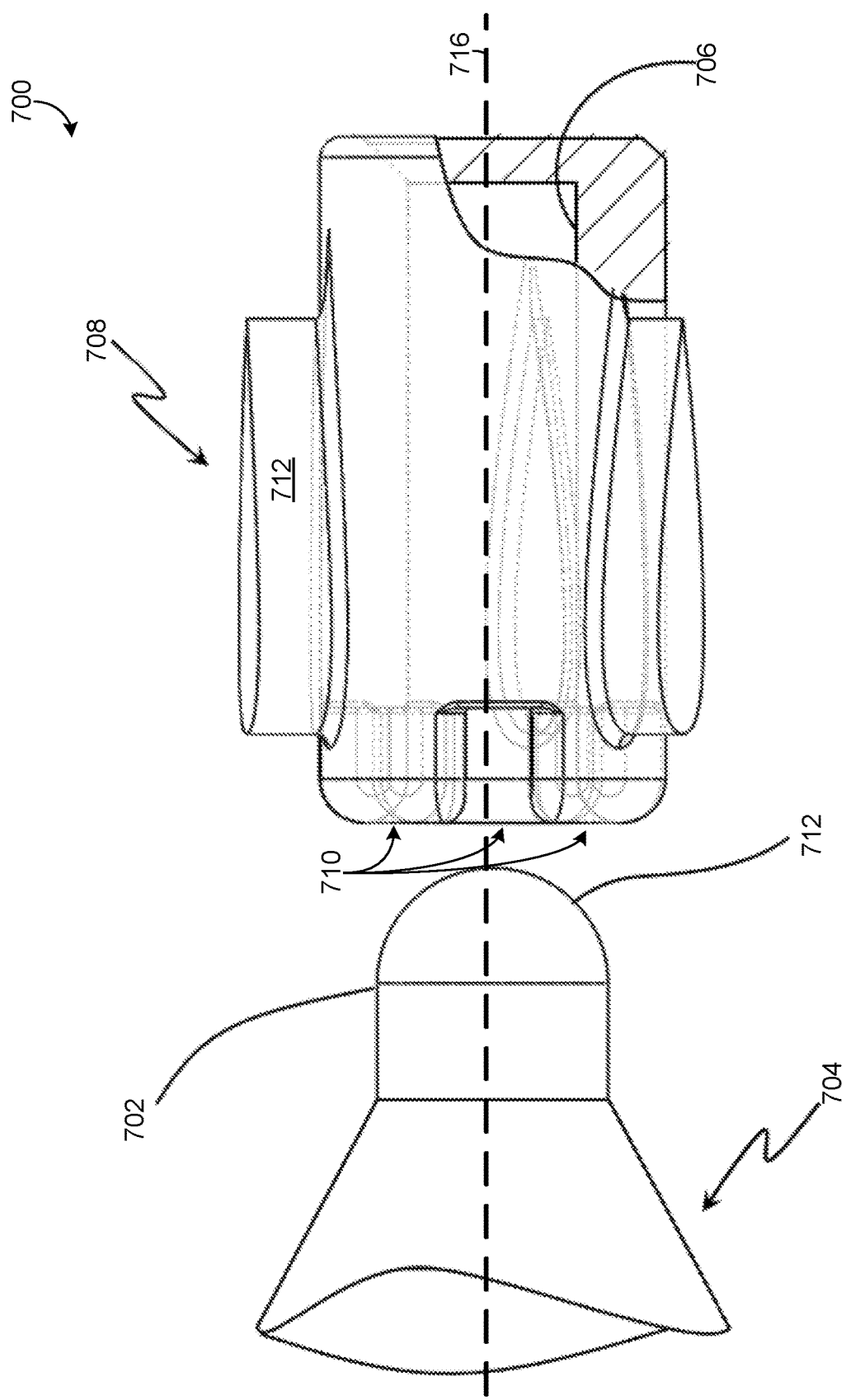
FIG. 7 shows a side view of a mechanical bearing for a blood pump.

FIG. 7 shows a side view of a mechanical bearing 700 for a blood pump (e.g., blood pump 100 of FIGS. 1A-1B and blood pump 300 of FIG. 3). Mechanical bearing 700 is similar to mechanical bearing 500, and so, for brevity, the differences will be described below.

Mechanical bearing 700 includes a bearing cone 702 comprising a ceramic surface 712. The cone 702 can include the various geometries described above, such as a pin, conical surface, spherical surface, etc., though an approximately spherical surface 712 is shown. The bearing cone 702 is affixed to a rotor 704 (e.g., rotor 104, 304, etc.) that is configured to rotate substantially about axis 716.

The mechanical bearing includes a cup 708. The cup 708 is configured to be stationary relative to the bearing cone 702 that rotates. The cup 708 is affixed to a housing of the blood pump, or another non-rotating portion of the blood pump. The cup 708 can be affixed to the housing by blades 712 (e.g., trunnions) that function similarly to blades 508 of FIG. 5. One or more washout passages 710 of the cup 708 are configured to direct blood flow away from the point of contact of the mechanical bearing 700. The washout passages 710 can be radially symmetric about the cup 708. The cup can be hollow and include an interior surface 706 that guides blood flow through the mechanical bearing 700, across the point of contact of surface 712 with cup 708 and out washout passages 710.

Figure 8A:
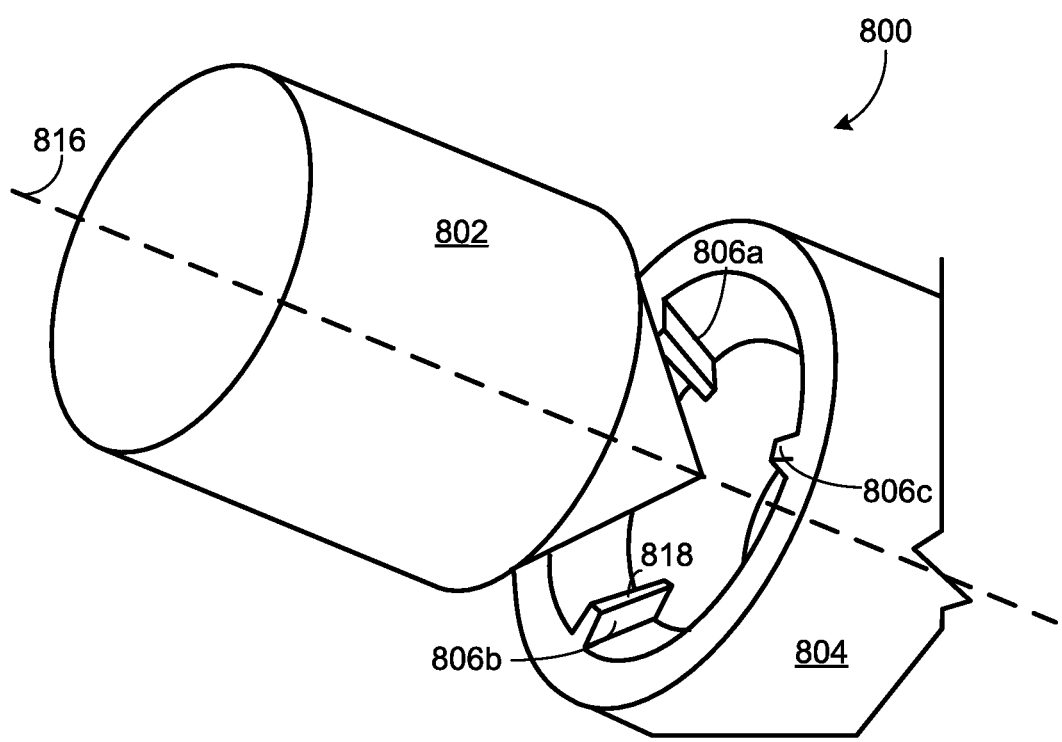
FIGS. 8A-8B show perspective views of a mechanical bearing for a blood pump.
Figure 8B:
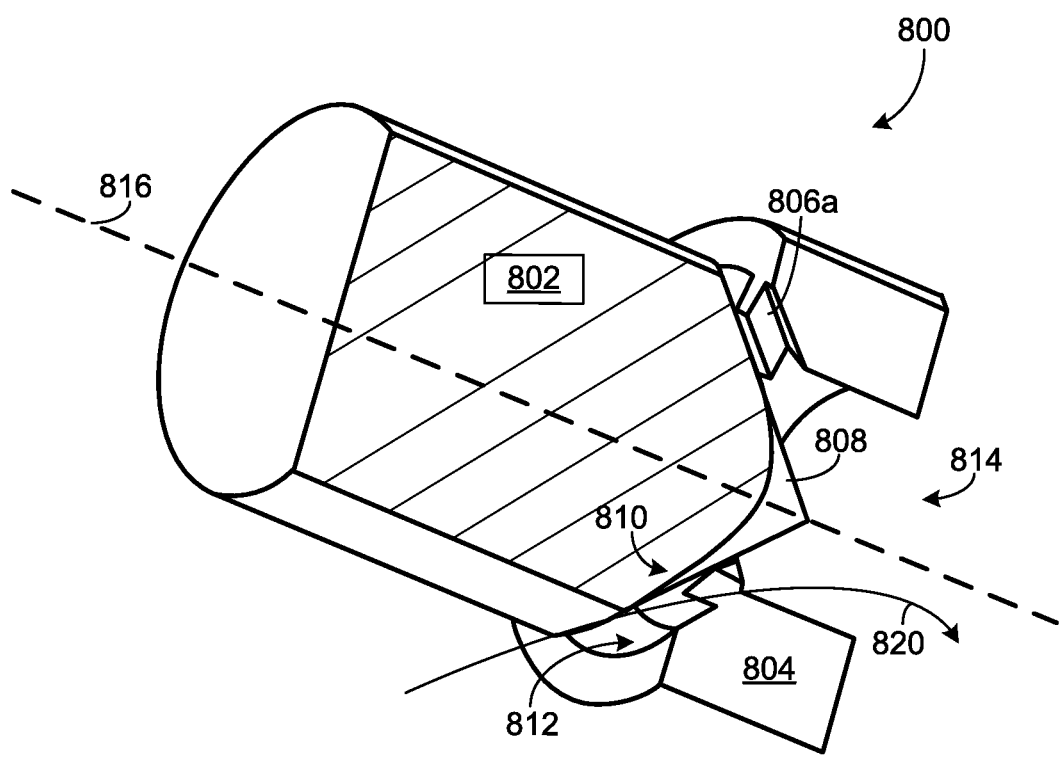

FIGS. 8A-8B show perspective views of a mechanical bearing 800 for a blood pump (e.g., blood pump 100 of FIGS. 1A-1B, blood pump 300 of FIG. 3, etc.). Mechanical bearing 800 is similar to mechanical bearings 500 and 800, and so, for brevity, the differences will be described below.

Mechanical bearing 800 includes a bearing pin 802 and a bearing cup 804. The bearing pin 802 is similar to bearing pin 502 and includes a conical surface 808. In some implementations, the bearing pin 802 includes a ceramic surface, and in some implementations, the bearing pin 802 is fabricated from a ceramic material. The bearing pin 802 is configured to couple with the bearing cup 804 and rotate about axis 816. The bearing pin 802 is affixed to a rotor.

The bearing cup 804 is configured to receive the bearing pin 802 and provide axial support (e.g., thrust support) for the bearing pin during operation of a blood pump including the mechanical bearing 800. The bearing cup 804 includes a plurality of trunnions 806a, 806b, 806c (collectively trunnions 806) for supporting the bearing pin 802. The trunnions 806 are angled to support a similarly angled surface 808 of the bearing pin 802. Each trunnion 806a-c forms a point of contact 810 with the bearing pin 802. While three trunnions 806 are shown, a greater number of trunnions (four, five, six, seven, etc.) can be used. In some implementations, the trunnions 806 each include a rounded upper surface (e.g., surface 818) that contacts surface 808. The rounded surface minimizes the area of contact between bearing pin 802 and bearing cup 804. In some implementations, the bearing cup 804 includes a ceramic surface, and in some implementations, the bearing cup 804 is fabricated from a ceramic material.

The mechanical bearing 800 includes a plurality of points of contact 810, one for each trunnion 806a-c. The points of contact are near the axis 816 to minimize a linear velocity between the bearing pin 802 and the bearing cup 804 and thus minimize heat generation of the mechanical bearing 800. The bearing cup 804 includes an annular opening 814 that allows blood flow over the points of contact 810 and lubricate the mechanical bearing 800. The trunnions 806 are each sized at a height from the bearing cup 804 to allow a gap 812 to persist between the bearing pin 802 and the bearing cup when the bearing pin is coupled with the bearing cup. The gap 812 functions as a washout channels between each of the trunnions 806. The gap 812 guides blood flow away from the mechanical bearing 800 and reduce stagnant blood flow (e.g., vortices) near the points of contact 810. An example approximate blood flow path is shown by arrow 820.

FIG. 9A shows a side view of an example blood pump 900 including a bearing system. FIG. 9B shows a close-up side view of a mechanical bearing 950 of the blood pump of FIG. 9A. Blood pump 900 is substantially similar to blood pump 100, but includes a different mechanical bearing 932 (seen in detail in FIG. 9B). Further, the mechanical bearing 932 is near the inlet 934 rather than the outlet 936. Specifically, the mechanical bearing 932 is between the rotor 904 and the inlet 934, rather than between the rotor and the outlet 936. The blood pump 900 is configured to pump fluid (e.g., blood) from inlet 934 to outlet 936. Outlet 936 is approximately axially aligned with inlet 934 on axis 916. The rotor 904 is configured to rotate substantially about axis 916, shown by arrow 910. Motor coils 912 drive rotation of the rotor 904 using electromagnets 922 and back irons 914 in a similar manner as the rotor 104 of FIGS. 1A-1B is rotated. Magnetic bearing formed from permanent magnet stacks 908a (outer race), 908b (inner race) supports the rotor body 918 radially with respect to axis 916, and stabilize pitch and yaw motion directions of the rotor 904 with respect to axis 916. Blood flow paths 924, 926 form a radial path around the rotor 904 through the housing 902 of the blood pump 900. The magnetic bearing 908 works in combination with the mechanical bearing 932 that provides thrust support to the rotor 904 along axis 916. As the rotor 904 drives blood along blood flow paths 924, 926 (e.g., by blades 928), a thrust force pushes the rotor nose 920 into trunnions 930. Blood flows through the mechanical bearing 932 between the trunnions 930 and the nose 920, lubricating the sliding bearing. The blood flows around the rotor 904 through the housing to the outlet 936. The outer surface of the rotor 904 has sharp forward and rear edges that promote laminar flow and washing of the mechanical bearing surfaces 930, reducing vortices and stagnant blood flow, and thus thrombosis formation. Stator blades 938 are provided to "unwind" the spiral blood flow path generated by the impeller, thereby recovering pressure. The blood thus flows across the rotor in a substantially laminar manner.

By comparison, FIGS. 10A-10B show a side view of an example blood pump 1000 (e.g., similar to blood pump 900 described in relation to FIGS. 9A-9B) including a non-axial (e.g., tangential) outlet 1010. FIG. 10B shows a close-up side view of a mechanical bearing 932 of the blood pump 1000 of FIG. 10A.

The blood pump 1000 is substantially similar to blood pump 900, except that the outlet 1010 is tangential to axis 916 rather than axially aligned with axis 916 and inlet 934. The housing 1002 closes off at rear, blunted end 1020 of a body 1018 of the rotor 1004. The rotor 1004 is configured to rotate about axis 916 and drive blood from the inlet 934 toward the blunted end 1020 of the rotor. The housing 1002 is curved to direct blood flow toward the tangential outlet 1010. In some implementations, the housing 1002 approximately follows an exterior shape of the blunted end 1020 of the rotor 1004, leaving a gap 1022 for blood flow.

A volute 1006 extends from the housing 1002 toward outlet 1010. Blades (not shown) can be added to the rotor 1004 (e.g., on the back side of the rotor near the outlet 1010) to direct blood flow toward the volute 1006 and out the blood pump 1000 outlet 1010.

FIG. 11 shows a process 1100 for pumping blood. A rotor rotates (1102) about an axis by an electromagnetic force, the rotor configured to drive blood substantially along the axis through the housing from an inlet of the housing to an outlet of the housing. The process includes supporting (1104) the rotor in the housing by a magnetic bearing comprising a permanent magnet and configured to provide radial support to the rotor. The process includes supporting (1106) the rotor in the housing by a sliding bearing configured to provide axial support to the rotor, wherein the sliding bearing is immersed in blood flow and wherein the sliding bearing comprises a washing surface configured to guide the blood flow away from the sliding bearing. The process includes controlling (1108) a thrust force on the rotor, a pitch angle of the rotor, and a yaw angle of the rotor during rotation of the rotor.

Various inventive features of a blood pump of this blood pump have been described above. It will be appreciated that not all inventive features need be combined in a single pump. Rather, some inventive features may be included within other pumps without using other inventive features. It is to be understood, however, that even though numerous characteristics and advantages of the present blood pump have been set forth in the foregoing description, together with details of the structure and function of the blood pump, the disclosure is illustrative only, and changes may be made in detail, especially in matters of shape, size and arrangement of parts within the principles of the blood pump to the full extent indicated by the broad general meaning of the terms in which the appended claims are expressed.

What is claimed is:

1. A blood pump, comprising:
   a housing comprising an inlet and an outlet, an axis of the housing being from the inlet to the outlet;
   a rotor disposed in the housing, the rotor configured to rotate substantially about the axis to pump blood from the inlet to the outlet, the axis being a central axis of rotation;
   a stator disposed within the housing and coupled to the housing, the stator configured to drive rotation of the rotor about the axis; and
   a bearing mechanism for supporting the rotor inside the housing, the bearing mechanism comprising:
      a magnetic bearing, comprising a permanent magnet and configured to magnetically support the rotor inside the housing in a radial direction from the axis, the magnetic bearing comprising a first suspension magnet affixed to the housing and a second suspension magnet affixed to the rotor; and
      a sliding bearing configured to physically support the rotor inside the housing in an axial direction along the axis of the housing and allow rotation of the rotor substantially about the axis, the sliding bearing comprising at least one point of contact where the rotor is configured to physically contact a plurality of trunnions affixed to the housing, wherein one or more trunnions of the plurality extend from a side of the housing toward the axis of rotation of the rotor without crossing the axis of rotation;
   wherein the sliding bearing comprises the plurality of trunnions, and wherein the plurality of trunnions are radially spaced in a blood flow path to allow blood to flow along the axis of rotation of the rotor and between the trunnions of the plurality of trunnions, wherein the blood flow path along the axis of rotation is from a first side of the sliding bearing through the sliding bearing along the axis of rotation to a second side of the sliding bearing, the second side being opposite the first side along the axis of rotation.

2. The blood pump of claim 1, wherein at least one trunnion of the plurality of trunnions comprises an arcuate surface configured to contact the rotor and physically support the rotor inside the housing in the axial direction along the axis of the housing and in the radial direction that is substantially orthogonal to the axial direction.

3. The blood pump of claim 1, wherein the sliding bearing comprises a flat surface of at least one trunnion of the plurality of trunnions, the at least one trunnion configured to contact a tapered point of the rotor and physically support the rotor inside the housing in the axial direction along the axis of the housing.

4. The blood pump of claim 1, wherein each trunnion of the plurality of trunnions comprises a concave surface configured to contact a curved surface of the rotor and physically support the rotor inside the housing in the axial direction along the axis of the housing and in the radial direction that is substantially orthogonal to the axial direction.

5. The blood pump of claim 1, wherein each trunnion of the plurality of trunnions comprises a bearing pin extending substantially along the axis, and wherein the rotor comprises a pointed end configured to contact the bearing pin, wherein the pointed end of the rotor is configured to align with the axis during rotation of the rotor.

6. The blood pump of claim 1, wherein each trunnion of the plurality of trunnions comprises a convex surface configured to engage the rotor at a respective point of contact, and wherein blood is configured to flow across the convex surface of each trunnion during operation of the blood pump.

7. The blood pump of claim 1, wherein the rotor is configured to receive a thrust force in the axial direction when blood is flowing through the housing, and wherein the thrust force is configured to cause the rotor to physically engage at least one trunnion of the plurality of trunnions at the at least one point of contact of the sliding bearing.

8. The blood pump of claim 1, wherein the at least one point of contact between the rotor and at least one trunnion of the plurality of trunnions is configured to be submerged in the blood flow path from the inlet to the outlet; and
   wherein the at least one trunnion of the plurality of trunnions and the rotor each comprises one or more washout passages each configured to direct blood flow away from the at least one point of contact between the rotor and the at least one trunnion.

9. The blood pump of claim 1, wherein the sliding bearing is positioned between the inlet of the housing and the magnetic bearing.

10. The blood pump of claim 1, wherein the sliding bearing is positioned between the outlet of the housing and the magnetic bearing.

11. The blood pump of claim 1, wherein at least a portion of the rotor that is configured to contact at least one trunnion of the plurality of trunnions comprises a ceramic material.

12. The blood pump of claim 1, wherein the sliding bearing is seamless.

13. The blood pump of claim 1, wherein at least one trunnion of the plurality of trunnions comprises a hollow interior that allows blood to flow within the trunnion and over a contact surface of the trunnion with the rotor.

14. The blood pump of claim 1, the rotor comprising an inducer blade that extends from a rotor surface and that is configured to guide blood away from the sliding bearing and towards the outlet of the blood pump.

15. The blood pump of claim 1, wherein the bearing mechanism is configured to reduce thrombus formation by at least 25% inside the blood pump.

16. The blood pump of claim 1, wherein the bearing mechanism is configured to eliminate thrombus formation inside the blood pump.

17. A system for pumping blood, comprising:
   a blood pump comprising:

a housing comprising an inlet and an outlet, an axis of the housing being from the inlet to the outlet;

a rotor disposed in the housing, the rotor configured to rotate substantially about the axis to pump blood from the inlet to the outlet, the axis being a central axis of rotation;

a stator disposed within the housing and coupled to the housing, the stator configured to drive rotation of the rotor about the axis; and a bearing mechanism for supporting the rotor inside the housing, the bearing mechanism comprising:

a magnetic bearing, comprising a permanent magnet and configured to magnetically support the rotor inside the housing in a radial direction from the axis, the magnetic bearing comprising a first suspension magnet affixed to the housing and a second suspension magnet affixed to the rotor; and a sliding bearing configured to physically support the rotor inside the housing in an axial direction along the axis of the housing and allow rotation of the rotor substantially about the axis, the sliding bearing comprising at least one point of contact where the rotor is configured to physically contact a plurality of trunnions affixed to the housing, wherein one or more trunnions of the plurality extend from a side of the housing toward the axis of rotation of the rotor without crossing the axis of rotation;

wherein the sliding bearing comprises the plurality of trunnions, and wherein the plurality of trunnions are radially spaced in a blood flow path to allow blood to flow along the axis of rotation of the rotor and between the trunnions, wherein the blood flow path along the axis of rotation is from a first side of the sliding bearing through the sliding bearing along the axis of rotation to a second side of the sliding bearing, the second side being opposite the first side along the axis of rotation; and a controller configured for communication with the magnetic bearing and configured to provide a control signal to the magnetic bearing to produce a correcting force on the rotor that is configured to align an axis of the rotor with the axis of the housing, wherein the rotor is configured to maintain the at least one point of contact with the each of the plurality of trunnions while experiencing the correcting force.

18. The system of claim 17, further comprising a position sensor affixed to the housing of the blood pump, the position sensor configured to provide a signal to the controller indicative of a positon of the rotor inside the housing, wherein the controller is configured to provide the control signal in response to receiving the signal from the position sensor.

19. A blood pump, comprising:

a housing comprising an inlet and an outlet, the outlet being tangential to an axis of rotation defined by the inlet;

a rotor disposed in the housing, the rotor configured to rotate substantially about the axis to pump blood from the inlet to the outlet, wherein the rotor comprises one or more blades configured to direct blood flow toward the outlet;

a stator disposed within the housing and coupled to the housing, the stator configured to drive rotation of the rotor about the axis; and a bearing mechanism for supporting the rotor inside the housing, the bearing mechanism comprising:

a magnetic bearing comprising a permanent magnet and configured to magnetically support the rotor inside the housing in a radial direction from the axis, the magnetic bearing comprising a first suspension magnet affixed to the housing and a second suspension magnet affixed to the rotor; and a sliding bearing configured to physically support the rotor inside the housing in an axial direction along the axis of the housing and allow rotation of the rotor substantially about the axis, the sliding bearing comprising at least one point of contact where the rotor is configured to physically contact a plurality of trunnions affixed to the housing, wherein one or more trunnions of the plurality extend from a side of the housing toward the axis of rotation of the rotor without crossing the axis of rotation;

wherein the sliding bearing comprises the plurality of trunnions, and wherein the plurality of trunnions are radially spaced in a blood flow path to allow blood to flow along the axis of rotation of the rotor and between the trunnions of the plurality of trunnions, wherein the blood flow path along the axis of rotation is from a first side of the sliding bearing through the sliding bearing along the axis of rotation to a second side of the sliding bearing, the second side being opposite the first side along the axis of rotation.

20. A method of pumping blood comprising:

rotating a rotor about an axis of rotation by an electromagnetic force, the rotor configured to drive blood substantially along the axis through a housing from an inlet of the housing to an outlet of the housing;

supporting the rotor in the housing by a magnetic bearing comprising a permanent magnet and configured to provide radial support to the rotor;

supporting the rotor in the housing by a sliding bearing configured to provide axial support to the rotor, wherein the sliding bearing is immersed in blood flow and wherein the sliding bearing comprises a washing surface configured to guide the blood flow away from the sliding bearing, wherein the sliding bearing comprises a plurality of trunnions affixed to the housing, wherein one or more trunnions of the plurality extend from a side of the housing toward the axis of rotation of the rotor without crossing the axis of rotation;

wherein the sliding bearing comprises the plurality of trunnions, and wherein the plurality of trunnions are radially spaced in a blood flow path to allow blood to flow along the axis of rotation of the rotor and between the trunnions of the plurality of trunnions, wherein the blood flow path along the axis of rotation is from a first side of the sliding bearing through the sliding bearing along the axis of rotation to a second side of the sliding bearing, the second side being opposite the first side along the axis of rotation; and controlling, by a controller, a thrust force on the rotor, a pitch angle of the rotor, and a yaw angle of the rotor during rotation of the rotor.

* * * * *